US011639377B2

(12) United States Patent
Xu et al.

(10) Patent No.: US 11,639,377 B2
(45) Date of Patent: May 2, 2023

(54) PREPARATION OF TYPE I COLLAGEN-LIKE FIBER AND METHOD FOR REGULATING AND CONTROLLING THE D-PERIODIC OF FIBER THEREOF

(71) Applicants: Jiangnan University, Wuxi (CN); Rutgers University, Piscatway, NJ (US)

(72) Inventors: Fei Xu, Wuxi (CN); Jinyuan Hu, Wuxi (CN); Vikas Nanda, Wuxi (CN); David I. Shreiber, Wuxi (CN); Meng Zhang, Wuxi (CN); Sonal Gahlawat, Wuxi (CN)

(73) Assignees: JIANGNAN UNIVERSITY, Wuxi (CN); RUTGERS UNIVERSITY, Piscatway, NJ (US)

( * ) Notice: Subject to any disclaimer, the term of this patent is extended or adjusted under 35 U.S.C. 154(b) by 112 days.

(21) Appl. No.: 17/082,525

(22) Filed: Oct. 28, 2020

(65) Prior Publication Data

US 2021/0079064 A1   Mar. 18, 2021

(30) Foreign Application Priority Data

Apr. 23, 2020  (CN) .......................... 202010325899.X
Apr. 23, 2020  (CN) .......................... 202010327199.4

(51) Int. Cl.
*C07K 14/52* (2006.01)
*C07H 21/04* (2006.01)
*C12N 5/02* (2006.01)
*C12N 1/20* (2006.01)
*C12N 15/00* (2006.01)
*C07K 14/78* (2006.01)

(52) U.S. Cl.
CPC .................................... *C07K 14/78* (2013.01)

(58) Field of Classification Search
None
See application file for complete search history.

(56) References Cited

U.S. PATENT DOCUMENTS

| 2013/0164286 A1* | 6/2013 | Chou ...................... A61P 29/00 435/328 |
| 2017/0355748 A1 | 12/2017 | Raines et al. |
| 2018/0236141 A1* | 8/2018 | Russell ...................... A61K 9/08 |

FOREIGN PATENT DOCUMENTS

| GN | 1371919 A | 10/2002 | |
| GN | 105764920 A | 7/2016 | |
| WO | WO-2014146175 A1 * | 9/2014 | .............. C07K 1/145 |
| WO | WO-2015031950 A1 * | 3/2015 | .............. A61K 8/65 |
| WO | 2017020025 A1 | 2/2017 | |

OTHER PUBLICATIONS

Yoshizumi et al. Self-association of *Streptococcus pyogenes* collagen-like constructs into higher order structures. Protein Science 2009 vol. 18:1241-1251. (Year: 2009).*
Peng et al. A *Streptococcus pyogenes* derived collagen-like protein as a non-cytotoxic and non-immunogenic cross-linkable biomaterial. Biomaterials. Apr. 2010 ; 31(10): 2755-2761. (Year: 2010).*
Boudko et al. Trimerization and Triple Helix Stabilization of the Collagen XIX NC2 Domain. JBC, 283(49):34345-34351, 2008. (Year: 2008).*
Chopra et al. Conformational implications of enzymatic proline hydroxylation in collagen. Proc. Natl. Acd. Sci, USA, 79:7180-7184, 1982. (Year: 1982).*
Van Den Bergh et al. The NC16A domain of collagen XVII plays a role in triple helix assembly and stability. Biochem Biophys Res Commun. Dec. 1, 2006; 350(4): 1032-1037. (Year: 2006).*
Peng et al. Towards scalable production of a collagen-like protein from *Streptococcus pyogenes* for biomedical applications. Microbial Cell Factories, 2012, 11(146):1-8. (Year: 2012).*
Hwang et al. Folding Delay and Structural Perturbations Caused by Type IV Collagen Natural Interruptions and Nearby Gly Missense Mutations. JBC 287(6)4368-4375, 2012 and supplement material. (Year: 2012).*
Parmar et al. Harnessing the Versatility of Bacterial Collagen to Improve the Chondrogenic Potential of Porous Collagen Scaffolds. Adv Healthc Mater. Jul. 2016 ; 5(13): 1656-1666. (Year: 2016).*
An et al. Recombinant Collagen Engineered to Bind to Discoidin Domain Receptor Functions as a Receptor Inhibitor. JBC 291(9): 4343-4355, 2016. (Year: 2016).*
Yu et al. Dissecting a Bacterial Collagen Domain from *Streptococcus pyogenes*. Sequence and Length-Dependent Variations in Triple Helix Stability and Folding. J Biol Chem. May 27, 2011; 286(21): 18960-18968. (Year: 2011).*
Stoichevska et al. Formation of multimers of bacterial collagens through introduction of specific sites for oxidative crosslinking. J Biomed Mater Res Part A: 104A: 2369-2376, 2016. (Year: 2016).*
Zhuoxin Yua et. al. "Bacterial collagen-like proteins that form triple-helical structures" J Struct Biol. Jun. 2014 ; 186(3): 451 461.
Jennifer R. Litowski et. al. "Designing Heterodimeric Two-stranded alpha-Helical Coiled-coils" The Journal of Biological Chemistry vol. 277, No. 40, Issue of Oct. 4, pp. 37272 37279, 2002.

(Continued)

*Primary Examiner* — Maher M Haddad
(74) *Attorney, Agent, or Firm* — IPro, PLLC

(57) ABSTRACT

The disclosure discloses a preparation of type I collagen-like fibers and a method for regulating and controlling the periodic length of fiber stripes thereof, belonging to the technical field of genetic engineering. The disclosure produces a three-segment chimeric collagen P-CL-P pattern by inserting a continuous Gly-Xaa-Yaa triplet collagen sequence in the middle based on the N- and C-terminal $(GPP)_n$ sequences. The self-assembly is driven by the interaction between the N- and C-terminal $(GPP)_n$ triple helixes to form banded fibers with periodic bright and dark stripes. According to the method of the disclosure, a fiber from a clean source, which can self-assemble to form periodic bright and dark stripes can be prepared, the structure of which is similar to type I collagen, the preparation process is simple, the collagen fiber with low cost can be produced on a large scale, and the method has broad application prospects in the field of biological materials.

10 Claims, 15 Drawing Sheets
Specification includes a Sequence Listing.

(56) References Cited

OTHER PUBLICATIONS

Jens Friedrichs et al. Cellular Remodelling of Individual Collagen Fibrils.

Ayumi Yoshizumi et al. "Self-association of *Streptococcus pyogenes* collagen-like constructs into higher order structures" Protein Science 2009 vol. 18:1241-1251.

Lu C, Qiang S M, Sun T T, et al. Computational design of heterotrimeric collagen helices (in Chinese). Sci Sin Vitae, Science China Press, 2019, 49: 615 624, English Abstract only.

lucas c dunshee et. al. "Manipulation of the dually thermoresponsive behavior of peptide-based vesicles through modification of collagen-like peptide domains" Bioeng Transl Med, vol. 5(1), 2020;5:e10145. 20200131.

Ohm D. Krishna et. al. "Supramolecular assembly of electrostatically stabilized, hydroxyproline-lacking collagen-mimetic peptides" Biomacromolecules, vol. 10(9), Sep. 14, 2009.

1. Fratzl, P., Collagen: Structure and Mechanics, Chapter 1 Collagen: Structure and Mechanics, an Introduction, Springer, Boston, MA, 2008, pp. 1 to 13.

David L. Nelson, Michael M. Cox-Lehninger Principles of Biochemistry, 5th Edition—W. H. Freeman (2008). p. 124-125.

Li et al., Discerning the Subfibrillar Structure of Mineralized Collagen Fibrils: A Model for the Ultrastructure of Bone, PLoS ONE, 8(9):e76782, 2013.

Jiang et al., Feasibility Study of Tissue Transglutaminase for Self-Catalytic Cross-Linking of Self-Assembled Collagen Fibril Hydrogel and Its Promising Application in Wound Healing Promotion, ACS Omega, 4:12606-12615, 2019.

He et al., Extraction and Characterization of Self-Assembled Collagen Isolated from Grass Carp and Crucian Carp, Foods, 8:369, 2019.

Jin et al., A Biometric Hierarchical Nanointerface Orchestrates Macrophage Polarization and Mesenchymal Stem Cell Recruitment to Promote Endogenous Bone Regeneration, ACS Nano, 13:6581-6595, 2019.

Liu et al., Thermodynamically Controlled Self-Assembly of Hierarchically Staggered Architecture as an Osteoinductive Alternative to Bone Autografts, Adv. Funct. Mater., 1806445, 2019.

Hu et al., Design of synthetic collagens that assemble into supramolecular banded fibers as a functional biomaterial testbed, Nature Comm., 13:6761, 2022.

Friedrichs et al., Cellular Remodelling of Individual Collagen Fibrils Visualized by Time-lapse AFM, J. Mol. Biol., 372:594-607, 2007.

Zhou et al., Rationally Designed Redox-Sensitive Protein Hydrogels with Tunable Mechanical Properties, BioMacromolecules, 17(11):3508-3515, 2016.

Xu et al., Intermolecular channels direct crystal orientation in mineralized collagen, Nature Communications, 11:5068, 2020.

\* cited by examiner

PREPARATION OF TYPE I COLLAGEN-LIKE FIBER AND METHOD FOR REGULATING AND CONTROLLING THE D-PERIODIC OF FIBER THEREOF

This application was filed electronically via EFS-Web and includes an electronically submitted sequence listing in .txt format. The .txt file contains a sequence listing entitled "seq.txt" created on Aug. 10, 2022 and is 48 kilobytes in size. The sequence listing contained in this .txt file is part of the specification and is hereby incorporated by reference herein in its entirety.

TECHNICAL FIELD

The disclosure relates to a preparation of type I collagen-like fiber and a method for regulating and controlling the periodic length of fiber stripes thereof, belonging to the technical field of genetic engineering.

BACKGROUND

Collagen is a kind of biological polymer, and is of a tripe helix structure formed by three chains intertwined. Collagen can be divided into 28 types according to its gene sequence and functional role, the most important of which is type I collagen. In higher biological cells, after a series of maturation processes such as translation, modification, folding, and cutting of the proprotein of type I collagen, multiple collagen triple helices (collagen for short) are in staggered arrangement to form collagen fibers with uniform spacing and having bright and dark stripes (FIG. 1), whose morphology plays a key role in cell adhesion and growth [1], which are also biomaterials that promote the repair and regeneration of human tissues and organs.

Type I collagen is mainly used in the wound dressing for the treatment of skin burn, hemostatic sponges in surgical and dental operations, bone defect fillers and other biomedical materials. It is also widely used in the cosmetics and food industries and has a huge market demand. At present, type I collagen products on the market are mainly derived from animal skin, achilles tendon and other connective tissues. Its main advantages are high biocompatibility and easy absorption by the human body, but it is easy to contaminant by animal borne diseases such as prion. In order to improve the biosafety of collagen materials, how to prepare a type I collagen from a clean source is a concern in the field of biomedical materials.

At present, there are mainly three preparation methods: (1) chemical synthesis of collagen-like polypeptides, (2) heterologous expression of recombinant collagen in prokaryotic and eukaryotic microbial hosts, and (3) heterologous expression in higher biological hosts, such as cultivation of transgenic plants and animal cell culture. Although the chemically synthesized collagen-like polypeptide has the advantages such as high purity and easy modification of functional groups, the preparation cost is too high, which is not conducive to large-scale production. The common problems of transgenic plants and mammalian cell expression systems are harsh culture conditions, low expression levels, and long production cycles. Microbial expression systems have obvious advantages such as low cost and high expression levels. Current research shows that more and more mammalian and bacterial collagens have been proven to be heterologously expressed with high efficiency in hosts such as bacteria and yeast, and are correctly folded into collagen triple helices. Recombinant collagen has potential applications in the production of biomaterials, but it lacks the driving force for self-assembly to form a higher order structure and cannot form collagen fibers, which limits its application in biomaterials and tissue engineering. According to Barbara Brodsky et al., the collagen region after excision of the globular guide folding domain can be self-assembled into fiber through expressing full-length and double-length *Streptococcus pyogenes* collagen-like protein (Scl2), and increasing the length of the sequence can promote the self-assembly ability, but these recombination collagen sequences cannot form nanofiber morphology with regular bright and dark stripes similar to natural collagen [2].

REFERENCES

1. Friedrichs, J., A., et al., Cellular Remodelling of Individual Collagen Fibrils Visualized by Time-lapse AFM. Journal of Molecular Biology, 2007. 372(3): p. 594-607.
2. Yoshizumi, A., et al., Self-association of *Streptococcus pyogenes* collagen-like constructs into higher order structures. Protein Science, 2009. 18(6): p. 1241-1251.

SUMMARY

The present application promotes the highly polymerized self-assembly of collagen to form collagen fibers by fusion expression of $(GPP)_n$ at the N-terminus and C-terminus of collagen from different sources.

The disclosure provides a method for preparing a type I collagen-like fiber, comprising the following steps:
(1) synthesizing a gene encoding a single chain of type I collagen-like;
(2) connecting the gene synthesized in step (1) to a vector, transforming into a target cell for expression and purification;
(3) adding trypsin to a purified product in step (2), and reacting at the temperature of 25° C. for at least 6 h to obtain type I collagen-like;
(4) formulating collagen obtained in step (3) into a solution with a concentration of 0.1 to 1 mmol/L, and allowing to stand at 2° C. to 37° C.

In one embodiment, the single protein chain of the protein has an amino acid sequence as shown in

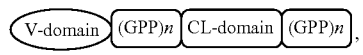, wherein an amino acid sequence of V-domain is shown in SEQ ID NO. 1; in $(GPP)_n$, n>5; and an amino acid sequence of CL-domain is shown in any one of SEQ ID NOs. 2-6.

In one embodiment, the V-domain and $(GPP)_n$ are connected through LVPRGSP (SEQ ID NO:33).

In one embodiment, n in $(GPP)_n$ satisfies 5<n≤30.

In one embodiment, an anterior end of the V-domain is also fused with 6×His tags.

In one embodiment, the gene encoding a single chain of type I collagen-like contains a nucleotide sequence shown in any one of SEQ ID NOs. 13-18.

In one embodiment, the vector described in step (2) is a plasmid.

In one embodiment, the plasmids include, but are not limited to: pColdIII series and pET series plasmids.

In one embodiment, the plasmid is pColdIII.

In one embodiment, the cells described in step (2) are *E. coli* cells, including but not limited to *E. coli* BL21, *E. coli* BL21 (DE3), *E. coli* JM109, *E. coli* DH5a or *E. coli* TOP10.

In one embodiment, the type I collagen-like is of a triple helix structure formed by three single protein chains coiling around a common central axis; the amino acid arrangement of the single protein chains is:

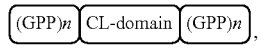, wherein, n in $(GPP)_n$ satisfies $5<n\leq30$, and an amino acid sequence of CL-domain is shown in any one of SEQ ID NOs. 2 to 6.

In one embodiment, the preparation method comprises the following steps:
(1) construction of collagen recombinant plasmid: synthesizing a gene v-$P_{10}AP_{10}$ encoding collagen as shown in SEQ ID NO. 13, a gene v-$P_{10}BP_{10}$ encoding collagen as shown in SEQ ID NO. 14, a gene v-$P_{10}CP_{10}$ encoding collagen as shown in SEQ ID NO. 15, a gene v-$P_{10}B_2P_{10}$ encoding collagen as shown in SEQ ID NO. 16, a gene v $P_{10}ABCP_{10}$ encoding collagen as shown in SEQ ID NO. 17, and a gene v-$P_{10}HP_{10}$ encoding collagen as shown in SEQ ID NO. 18, and connecting the synthesized genes to the plasmid pColdIII-Tu, respectively, wherein the pColdIII-Tu is constructed by mutating the pColdIII plasmid with pCOLD-TU(Nco I)-S: CTCGAGGGATCCGAATTCA (as shown in SEQ ID NO. 23) and pCOLD-TU(Nco I)-A: GAGCTCCATGGGCACTTTG (as shown in SEQ ID NO. 24) as primers to introduce the Nco I site;
(2) transformation: transforming the recombinant plasmids connected with any gene of SEQ ID NOs. 13-18 into E. coli BL21 (DE3), respectively;
(3) induction of expression: culturing the single colony of the positive transformant constructed in step (2) in a LB liquid medium overnight, and then transferring to a TB liquid medium at 1% inoculum size, culturing at 37° C. for 24 h, adding IPTG, inducing at 25° C. for 10 h, then adjusting the temperature to 15° C. and inducing for 14 h to obtain a cell culture solution.
(4) purification: collecting cell pellets in the cell culture solution of step (3), resuspending the cell pellets in phosphate buffer, lysing the cells with an ultrasonic cell disruptor under ice bath conditions, then centrifuging at 10,000 rpm at 4° C. for 20 min to remove cell debris, and then filtering the supernatant with a microporous filter membrane to remove impurities; injecting the sample into a His-trap hp affinity chromatography column (5 mL) installed in a protein purifier, and then washing 8 column volumes with the washing solution, eluting the protein with an elution buffer in which the imidazole content increases stepwise (140 mM, 400 mM), collecting protein fractions, digesting with trypsin, dialyzing, and freeze-drying; and
(5) formulating the freeze-dried collagen in step (4) into a solution with a concentration of 0.5 mmol/L, and allowing to stand at 4° C.-37° C. for at least 2 days.

The disclosure also provides collagen fibers prepared by applying the method; the collagen fibers are formed by self-assembly of the type I collagen-like, and have a morphology of bright and dark stripes when observed under an electron microscope.

In one embodiment, the collagen fibers are formed by highly polymerized self-assembly of the collagen.

In one embodiment, the standing time is not less than 24 h.

The disclosure also provides a method for regulating and controlling a periodic length of stripes of type I collagen-like, comprising introducing amino acid sequences of different sources or different lengths into a CL-domain region with a single protein chain as shown in

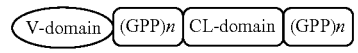

to regulate and control the length of the dark stripes; expressing the single protein chain by microorganisms, and collecting the expressed collagen with different lengths of dark stripes, wherein an amino acid sequence of V-domain is shown in SEQ ID NO. 1; in $(GPP)_n$, $n>5$; and the amino acid sequences of different lengths are amino acid sequences as shown in any one of SEQ ID NOs. 2-6, or multiple repeated sequences of any one of SEQ ID NOs. 2-6, or a combination of two or more of SEQ ID NOs. 2-6 in any order.

In one embodiment, the V-domain and $(GPP)_n$ are connected through LVPRGSP (SEQ ID NO:33).

In one embodiment, an anterior end of the V-domain is also fused with 6×His tags.

In one embodiment, the regulation and control specifically comprises introducing n glycine-proline-proline (GPP) in the $(GPP)_n$ region, so that the length of bright stripes reaches n×1 nanometers, where n is an integer greater than 5.

In one embodiment, the regulation and control comprises introducing an amino acid sequence as shown in any one of SEQ ID NOs. 2-6 in the CL-domain region, so that the dark stripes in the collagen fibers reach: (number of amino acids in the CL-domain region÷3×0.9)±1 nm.

In one embodiment, the regulation and control comprises introducing a collagen sequence having 81, 81×2, 81×3, and 108 amino acids in length in the CL-domain region, so that the dark stripes in the collagen fibers reach 24.0 nm, 47.4 nm, 72.3 nm and 32.6 nm in length.

In one embodiment, the regulation and control comprises introducing 1, 2, or 3 sequences as shown in SEQ ID NO. 2 in the CL-domain region, or introducing 1, 2, or 3 sequences as shown in SEQ ID NO. 3, or introducing 1, 2, or 3 sequences as shown in SEQ ID NO. 4, or introducing 1, 2 or 3 sequences as shown in SEQ ID NO. 5, so that the dark stripes in the collagen fibers reach 24.0 nm, 47.4 nm, and 72.3 nm in length.

In one embodiment, the regulation and control comprises introducing 1 or n sequences as shown in SEQ ID NO. 6 in the CL-domain region, so that the dark stripes in the collagen fibers reach 32.6 nm or n×32.6 nm in length, wherein, n is an integer greater than 1.

The disclosure also claims to protect application of the collagen, the genes, the plasmids, the cells or the preparation method in the biology, chemical industry, foods, medicines, biological materials, tissue engineering, cosmetics and other fields.

In one embodiment, the application is for preparing products containing collagen, including but not limited to preparing foods, medicines, biomedical materials, cosmetics, and the like.

Advantageous Effects

1. The disclosure produces a three-segment chimeric collagen P-CL-P pattern by inserting a continuous Gly-Xaa-Yaa triplet collagen sequence in the middle based on the N- and C-terminal $(GPP)_{10}$ sequences. The self-assembly is driven by the interaction between the N- and C-terminal (GPP)$_{10}$ triple helices to form banded fibers with periodic bright and dark stripes.

2. The disclosure precisely controls the periodic length of the bright and dark stripes of the fibers by adjusting the sequence length of the collagen region, and the sequence of the collagen region can be replaced. The collagen sequence involved in the disclosure is expressed by cold shock in *E. coli* to prepare fibers from a clean source, which can self-assemble to form periodic bright and dark stripes, the structure of which is similar to type I collagen, so that the preparation process is simple, and the collagen fiber with low cost can be produced on a large scale.

The disclosure provides a method for preparing type I collagen-like fibers and a sequence design mode thereof, wherein the collagen region of the sequence can be replaced and expanded, provides a platform for the research and application of periodic collagen fibers based on bright and dark stripes, and has broad prospects in the application of biological materials.

DETAILED DESCRIPTION

1. Technical Terms

Figure 1:
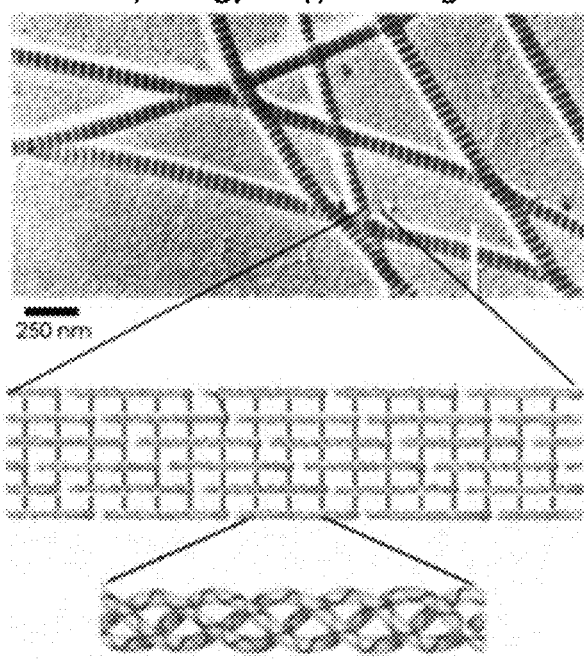
FIG. 1 shows the morphology of type I collagen fibers.

Unless otherwise specified, the "type I collagen-like" in this application refers to a triple helix structure formed by three single protein chains with periodic repetition (Gly-Xaa-Yaa)$_n$ coiling around a common central axis. The "type I collagen-like fiber" refers to a biological macromolecule with uniform spacing and a morphology of bright and dark stripes formed by the staggered arrangement, spontaneous aggregation or assembly of type I collagen-like.

2. Materials and Methods Used in the Disclosure

1) Media:

LB solid medium: 15 g/L agar, 10 g/L tryptone, 5 g/L yeast extract powder, 10 g/L NaCl, pH 7.0.

LB liquid medium: 10 g/L tryptone, 5 g/L yeast extract powder, 10 g/L NaCl, pH 7.0.

TB liquid medium: 12 g/L tryptone, 24 g of yeast extract powder, 4 mL glycerol, 2.31 g of KH$_2$PO$_4$, 12.54 g of K$_2$HPO$_4$, pH 7.5, diluting to 1 L.

2) Bacterial Culture Methods:

*E. coli* seed culture conditions: The LB liquid medium was inoculated with a single colony grown via a streak plate method, the medium loading volume was 10%, a 250 mL shake flask was used for culture, the culture temperature was 37° C., the culture time was 10 h, and the rotate speed was 200 rpm.

Fermentation and culture conditions of pET28a recombinant strains: A TB medium was used, the medium loading volume was 20%, the inoculum size was 1%, a 500 mL shake flask was used for culture, the culture temperature was 25° C., when OD$_{600}$ reached 2.5, IPTG with a final concentration of 1 mM was used for induction, the induction temperature was 35° C., the induction time was 24 h, and the rotate speed was 200 rpm.

Fermentation and culture conditions of pCold recombinant strains: A TB medium was used, the medium loading volume was 20%, the inoculum size was 1%, a 500 mL shake flask was used for culture, after culturing at 37° C. for 24 h, IPTG with a final concentration of 1 mM was used for induction, the induction was carried out at 25° C. for 10 h, then at 15° C. for 14 h, and the rotate speed was 200 rpm.

Example 1 Sequence Design and Collagen Preparation

A sequence was designed according to the structure as shown in

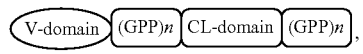

and the specific steps comprised:

(1) taking N- and C-terminal (GPP)$_{10}$ as fixed sequence motifs, inserting a variable collagen region in the middle to obtain a three-segment chimeric sequence

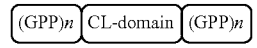

(abbreviated as P$_{10}$CLP$_{10}$). In this example, collagen Scl2 derived from *Streptococcus pyogenes* (Genbank ID: AAL50184.1) or an amino acid sequence (abbreviated as H) truncated from a human type I collagen α1 chain (UniProt ID: P02452.5) was used as a bacterial collagen for CL-domain, wherein the Scl2 collagen region was divided into three regions A, B, and C of equal length, and in the following examples, the designed CL domains were A, B, C, BB (two repeated B regions) and ABC (equivalent to the complete Scl2 collagen region), respectively; and (2) inserting the globular domain derived from Scl2 (as shown in SEQ ID NO. 1) at the N-terminus of the sequence to induce the correct folding of the collagen triple helix, and inserting a protease cleavage site LVPRGSP (SEQ ID NO:33) between the globular domain and the fixed sequence unit of the collagen region, and inserting 6×His at the N-terminus of the sequence for purification.

Amino acid sequences were designed as follows:

V-P$_{10}$AP$_{10}$ (as shown in SEQ ID NO. 7):
HHHHHHADEQEEKAKVRTELIQELAQGLGGIEKKNFPTLGDEDLDHTYMT

KLLTYLQEREQAENSWRKRLLKGIQDHALDLVPRGSPGPPGPPGPPGPPG

PPGPPGPPGPPGPPGPPGQDGRNGERGEQGPTGPTGPAGPRGLQGLQGFP

GERGEQGPTGPAGPRGLQGERGEQGPTGLAGKAGEAGAKGETGPAGPQGP

PGPPGPPGPPGPPGPPGPPGPPGPPG;

V-P$_{10}$BP$_{10}$ (as shown in SEQ ID NO. 8):
HHHHHHADEQEEKAKVRTELIQELAQGLGGIEKKNFPTLGDEDLDHTYMT

KLLTYLQEREQAENSWRKRLLKGIQDHALDLVPRGSPGPPGPPGPPGPPG

PPGPPGPPGPPGPPGPPGPRGEQGPQGLPGKDGEAGAQGPAGPMGPAGFP

GERGEKGEPGTQGAKGDRGETGPVGPRGERGEAGPAGKDGERGPVGPAGP

PGPPGPPGPPGPPGPPGPPGPPGPPG;

V-P$_{10}$CP$_{10}$ (as shown in SEQ ID NO. 9):
HHHHHHADEQEEKAKVRTELIQELAQGLGGIEKKNFPTLGDEDLDHTYMT

KLLTYLQEREQAENSWRKRLLKGIQDHALDLVPRGSPGPPGPPGPPGPPG

PPGPPGPPGPPGPPGPPGKDGQNGQDGLPGKDGKDGQNGKDGLPGKDGKD

GQNGKDGLPGKDGKDGQDGKDGLPGKDGKDGLPGKDGKDGQPGKPGPPGP

PGPPGPPGPPGPPGPPGPPGPPG;

V-P$_{10}$B$_2$P$_{10}$ (as shown in SEQ ID NO. 10):
HHHHHHADEQEEKAKVRTELIQELAQGLGGIEKKNFPTLGDEDLDHTYMT

KLLTYLQEREQAENSWRKRLLKGIQDHALDLVPRGSPGPPGPPGPPGPPG

PPGPPGPPGPPGPPGPPGPRGEQGPQGLPGKDGEAGAQGPAGPMGPAGFP

GERGEKGEPGTQGAKGDRGETGPVGPRGERGEAGPAGKDGERGPVGPAGP

RGEQGPQGLPGKDGEAGAQGPAGPMGPAGFPGERGEKGEPGTQGAKGDRG

ETGPVGPRGERGEAGPAGKDGERGPVGPAGPPGPPGPPGPPGPPGPPGPP

GPPGPPGPPG;

V-P$_{10}$ABCP$_{10}$ (as shown in SEQ ID NO. 11):
HHHHHHADEQEEKAKVRTELIQELAQGLGGIEKKNFPTLGDEDLDHTYMT

KLLTYLQEREQAENSWRKRLLKGIQDHALDLVPRGSPGPPGPPGPPGPPG

PPGPPGPPGPPGPPGPPGQDGRNGERGEQGPTGPTGPAGPRGLQGLQGLQ

GERGEQGPTGPAGPRGLQGERGEQGPTGLAGKAGEAGAKGETGPAGPQGP

RGEQGPQGLPGKDGEAGAQGPAGPMGPAGERGEKGEPGTQGAKGDRGETG

PVGPRGERGEAGPAGKDGERGPVGPAGKDGQNGQDGLPGKDGKDGQNGKD

GLPGKDGKDGQNGKDGLPGKDGKDGQDGKDGLPGKDGKDGLPGKDGKDGQ

PGKPGPPGPPGPPGPPGPPGPPGPPGPPGPPG;

V-P$_{10}$HP$_{10}$ (as shown in SEQ ID NO. 12):
HHHHHHADEQEEKAKVRTELIQELAQGLGGIEKKNFPTLGDEDLDHTYMT

KLLTYLQEREQAENSWRKRLLKGIQDHALDLVPRGSPGPPGPPGPPGPPG

-continued

PPGPPGPPGPPGPPGPPGPPGERGPPGPQGARGLPGAPGQMGPRGLPGERGRP

GAPGPAGARGEPGAPGSKGDTGAKGEPGPVGVQGPPGPAGEEGKRGARGE

PGPTGPAGPKGSPGEAGRPGEAGLPGPPGPPGPPGPPGPPGPPGPPGPPG

PPGPPG.

Genes encoding the above amino acid sequences were synthesized, wherein the nucleotide sequence encoding V-P$_{10}$AP$_{10}$ was shown in SEQ ID NO. 13; the gene sequence encoding V-P$_{10}$BP$_{10}$ was shown in SEQ ID NO. 14; the gene sequence encoding V-P$_{10}$CP$_{10}$ was shown in SEQ ID NO. 15; the gene sequence encoding V-P$_{10}$B$_2$P$_{10}$ was shown in SEQ ID NO. 16; the gene sequence encoding V-P$_{10}$ABCP$_{10}$ was shown in SEQ ID NO. 17; the nucleotide sequence encoding V-P$_{10}$HP$_{10}$ was shown in SEQ ID NO. 18; the nucleotide sequences shown above contained a 5' NcoI enzyme cleavage site, a 5' flanking sequence GC and 3' BamHI enzyme cleavage site, respectively. The above genes as synthesized were respectively inserted between the NcoI and BamHI of the pET28a and pCOLD III-Tu plasmids to obtain corresponding recombinant collagen plasmids, and then the recombinant plasmids were respectively transformed into *E. coli* BL21 (DE3) competent cells by a CaCl$_2$ method, plated on LB plates containing antibiotics, and cultured at 37° C., 200 rpm for 10 h. After screening, recombinant strains for preparing hybrid collagen were obtained; the pCOLD III-Tu plasmid was constructed by mutating the pCold Ill plasmid with the primers shown in SEQ ID NO. 23 and SEQ ID NO. 24 to introduce the Nco I site.

The recombinant strains were induced and fermented. The specific steps were as follows: a TB medium with a medium loading volume of 20% and an inoculum size of 1% was used and a 500 mL shake flask was used for culture, after culturing at 37° C. and 200 rpm for 24 h, IPTG with a final concentration of 1 mM was used for induction, the induction was carried out at 25° C. for 10 h, and then at 15° C. for 14 h. The induced cell culture solution was centrifuged at 8,000 rpm for 5 min to collect cells. The cells were resuspended in a phosphate buffer solution, the cells were lysed with an ultrasonic cell disruptor under ice bath conditions, then centrifuged at 10,000 rpm for 20 min at 4° C. to remove cell debris, and then the supernatant was filtered with a microporous filter membrane (0.45 μm) to remove impurities. The sample was injected into a 5 mL His-trap hp affinity chromatography column installed on a protein purifier, and then washed with a washing solution for 8 column volumes. The protein was eluted with an elution buffer in which the imidazole content increased stepwise (140 mM, 400 mM). The protein fractions were collected, and analyzed by SDS-PAGE electrophoresis. Then, the protein was digested with trypsin at a final concentration of 0.05 mg/mL at 25° C. for 6 h to excise the globular guide folding domain, and then desalted with a desalting column and freeze-dried to obtain freeze-dried collagen powder.

Figure 2A:
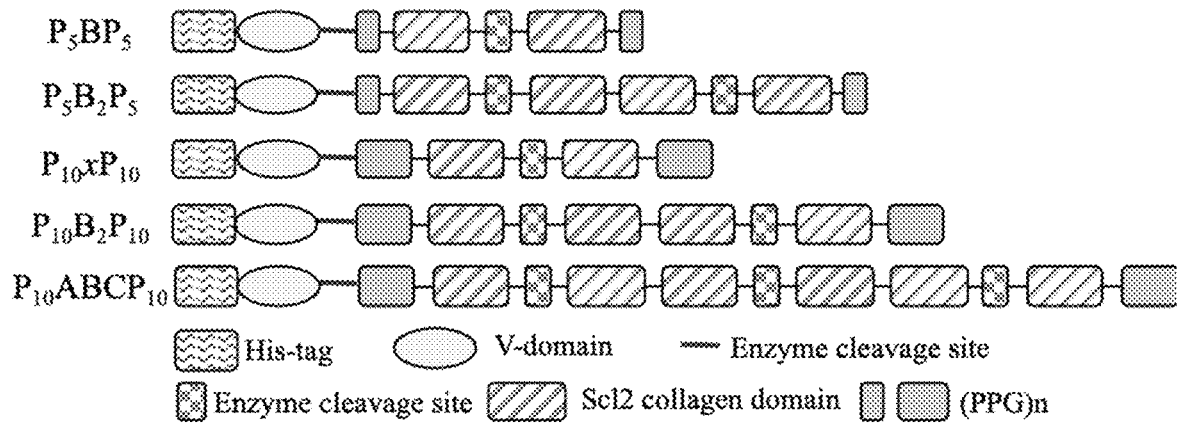
FIG. 2A is a schematic diagram of the three-segment chimeric sequence, x is sequence A, B, C or H.
Figure 2B:
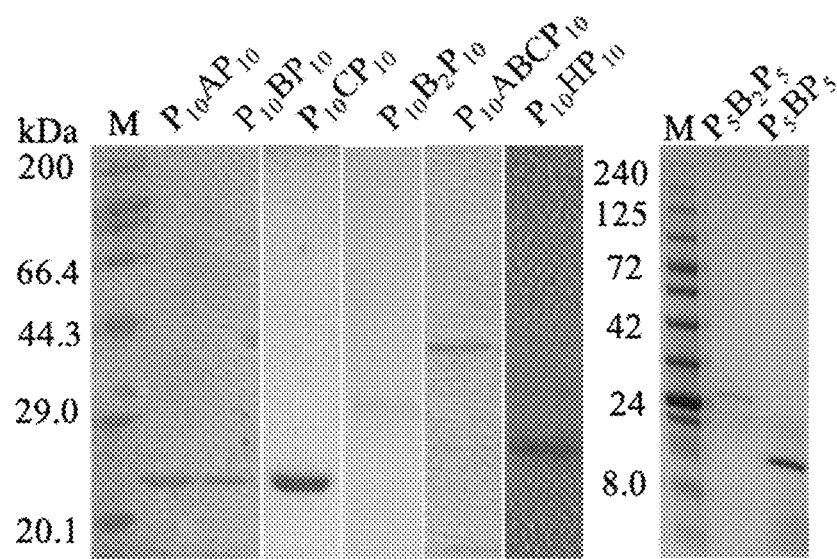
FIG. 2B is collagen SDS-PAGE after purification and enzyme cleavage.
Figure 3:
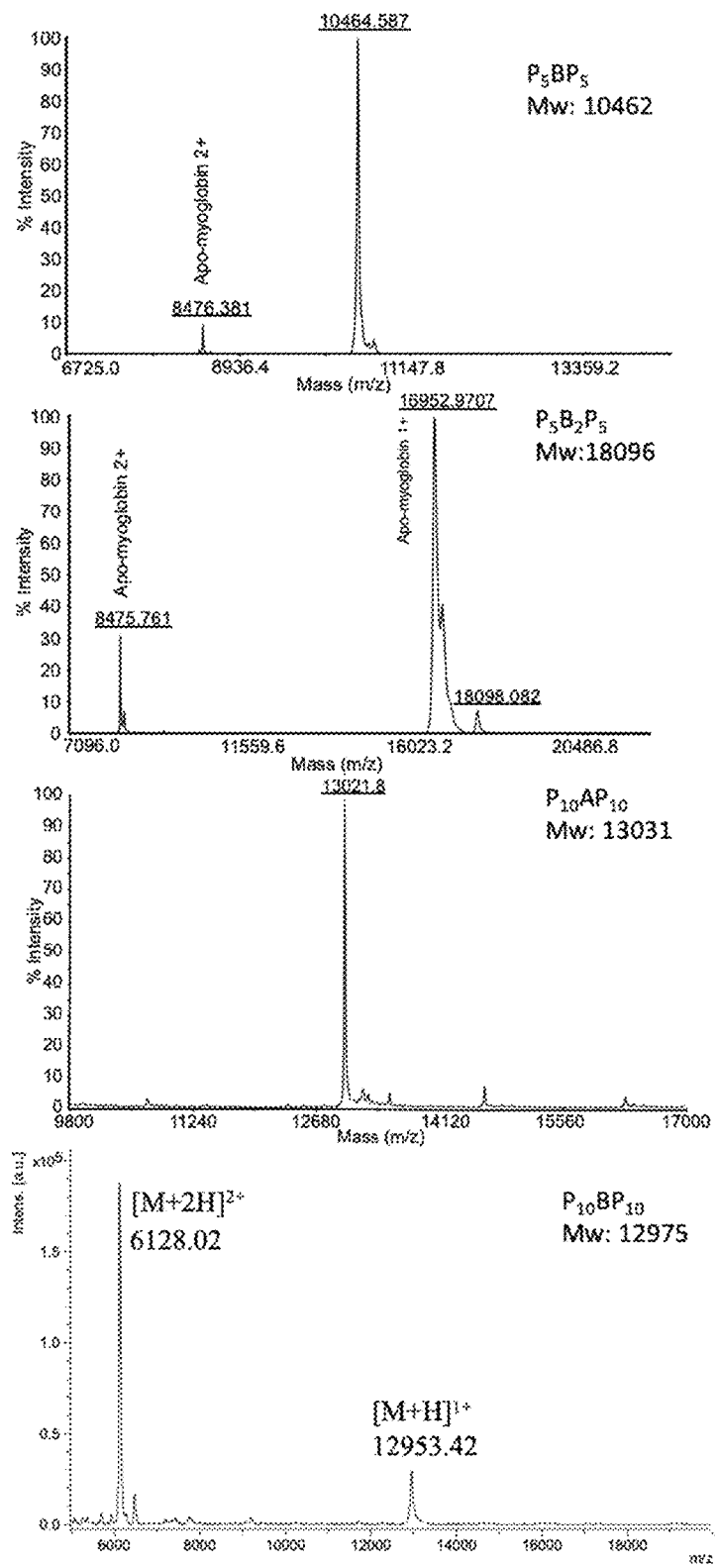
FIG. 3 shows MALDI-TOF molecular weight identification of the designed collagen.
Figure 3:
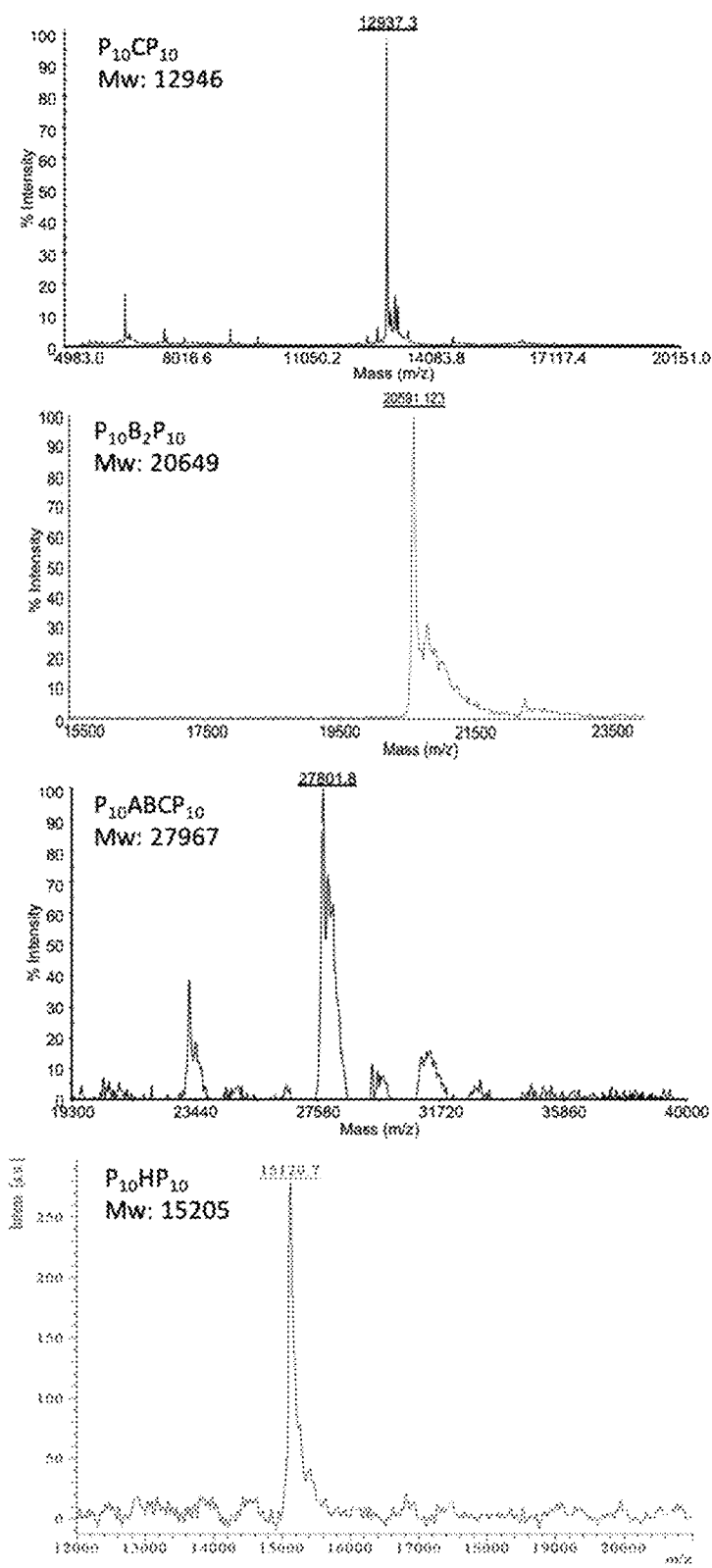

A small amount of freeze-dried powder was dissolved in water and identified by SDS-PAGE and Maldi-tof. FIG. 2 B shows that all of the digested protein has a single band detected by SDS-PAGE. Since collagen is a rod-shaped protein, the protein Marker used is a globular molecule, and the molecular weight shown by SDS-PAGE is greater than an expected molecular weight. As shown in FIGS. 3 A-(H), the molecular weight obtained by mass spectrometry is consistent with a theoretical molecular weight, and the collagen with a correct molecular weight is obtained.

Example 2 Determination of Secondary Structure of Collagen

The collagen prepared in Example 1 was formulated to a concentration of 1 mg/mL, and then allowed to stand at 4° C. for 24 h or more. A 1 mm cuvette was used to carry out the full-wavelength scan of the circular dichroism at 4° C., the wavelength range was from 190 nm to 260 nm, the wavelength interval was 1 nm, and retention time was 5 s at each wavelength. The thermo transition experiment was determined at 220 nm, the temperature range was from 4° C. to 80° C., the balance time was 8 s at each temperature, and the temperature increasing speed was 1° C./6 min. The typical CD spectrum of the triple helix structure of collagen shows a positive absorption peak at 220 nm.

Figure 4A:
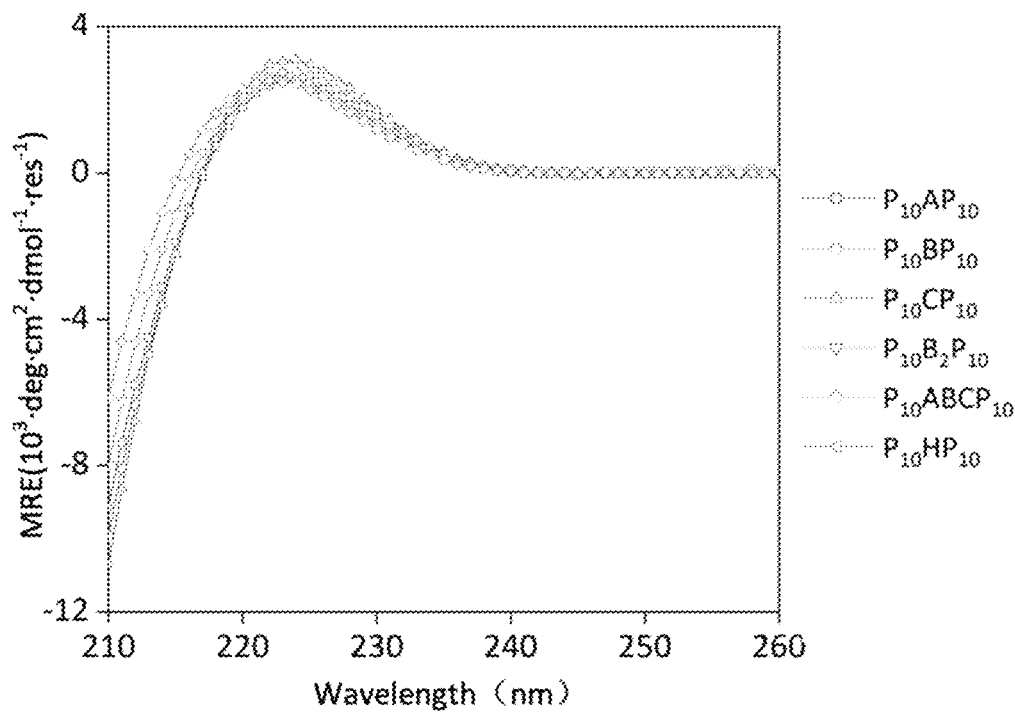
FIG. 4A is the full-wavelength scan spectrum of a circular dichroism.
Figure 4B:
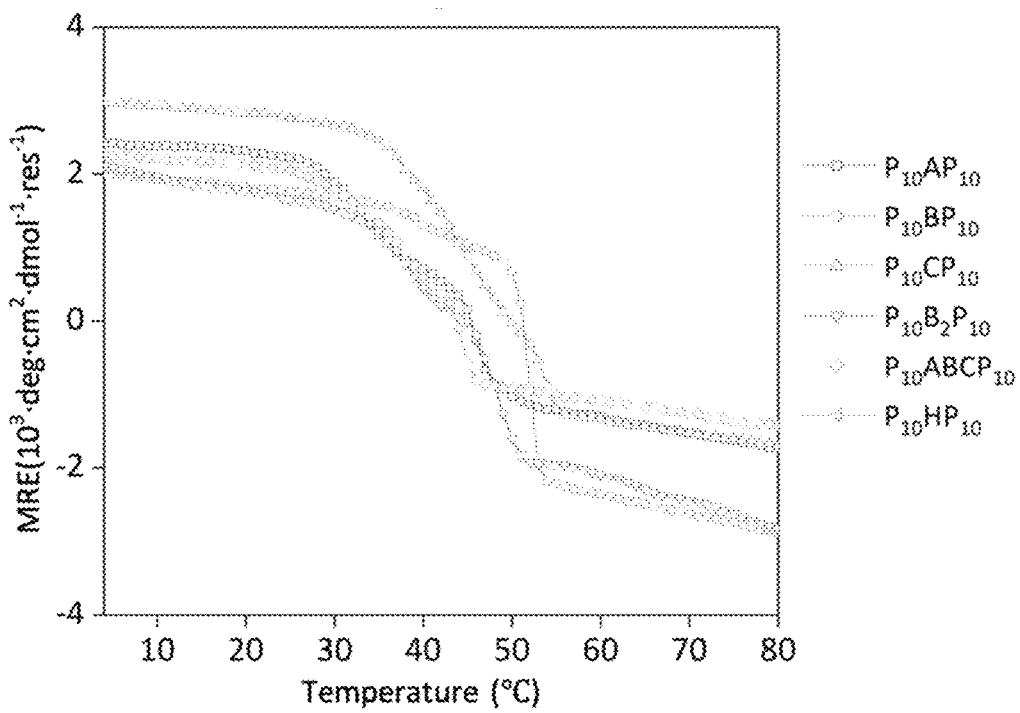
FIG. 4B is the thermo transition curve of the circular dichroism.

As shown in FIG. 4A and FIG. 4B, under full-wavelength scan, the protein designed in Example 1 has a characteristic absorption peak near 220 nm; the thermo transition experiment results show that the characteristic absorption value at 220 nm changes suddenly at about 50° C. with the increase of temperature, manifested by the destruction of the secondary structure of collagen and the unwinding of the triple helix. The CD full spectrum and the thermo transition experiment results show that the three-segment chimeric collagen designed in Example 1 can be correctly folded to form a collagen triple helix structure, and has a high thermal stability.

Example 3 the Regulation and Control of Fibrous Structure by Replacing Collagen Region Sequence The freeze-dried collagen $P_{10}AP_{10}$, $P_{10}BP_{10}$, $P_{10}CP_{10}$, and $P_{10}HP_{10}$ prepared in Example 1 were formulated into a solution with a final concentration of 0.5 mM with 10 mM PB and placed at 4° C. for 3.5 days. After that, a small amount of the solution was dropped on copper grids, after adsorption for 45 s, blot-dried with filter paper, then negatively stained with 0.75% phosphotungstic acid for 20 s, blot-dried with filter paper, and observed with a Hitachi H-7650 transmission electron microscope.

Figure 5A:
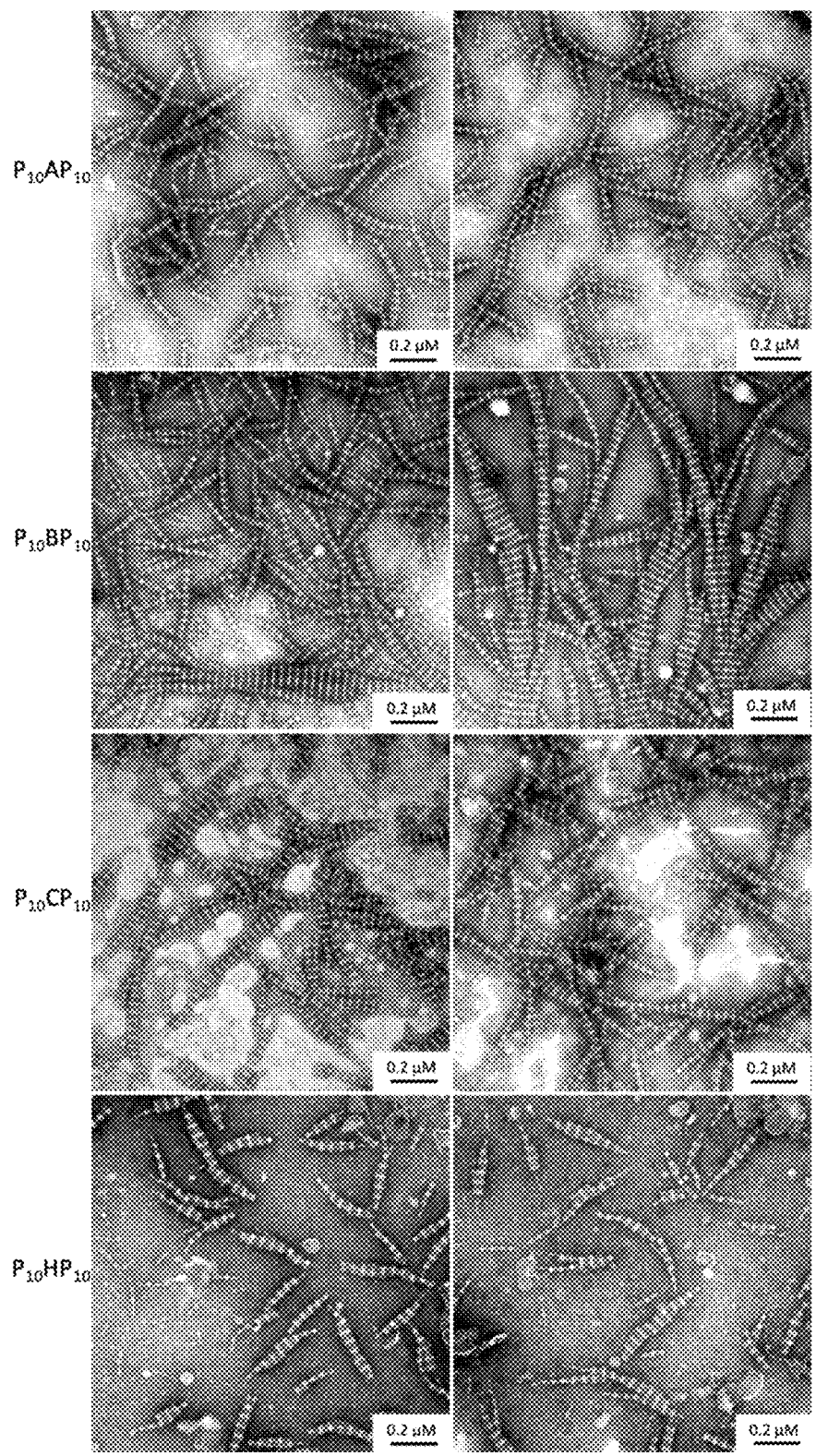
FIG. 5A are transmission electron micrographs of P$_{10}$CLP$_{10}$ self-assembled fibers.
Figure 5B:
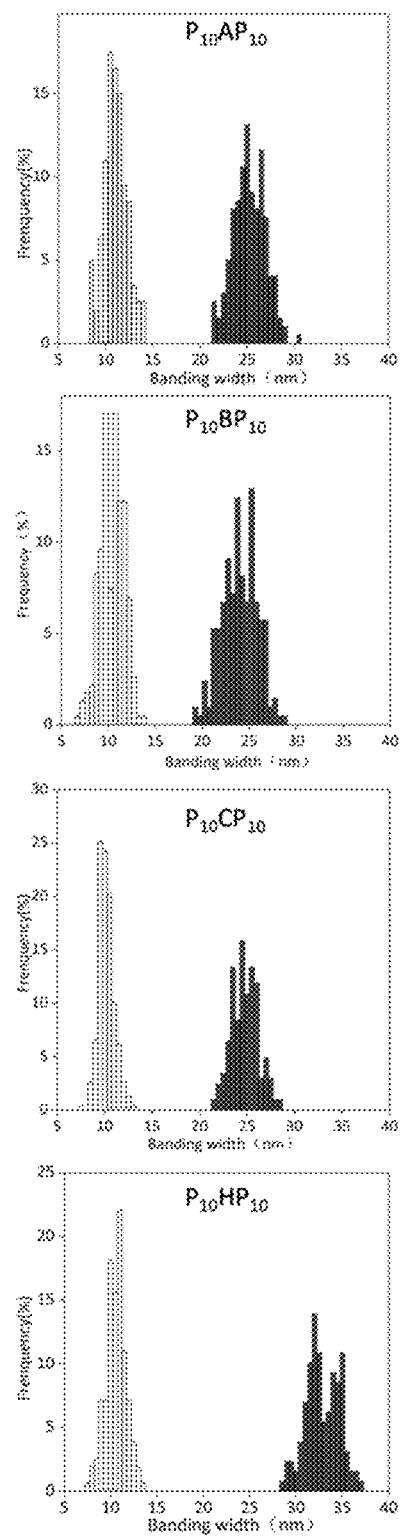
FIG. 5B are statistics of bright and dark stripes in length of the TEM results.

The transmission electron microscopy results shown in FIG. 5A show that all of the collagen designed in Example 1 can self-assemble to form banded fibers with periodic bright and dark stripes, and the periodic bright and dark stripes formed by sequences A, B and C have the same length. Through the measurement of the bright and dark stripes of the negatively stained $P_{10}BP_{10}$ fibers, and the statistics of at least 5 different TEM images and 200 or more sets of data, the lengths of the bright and dark stripes are found to be 10.4 nm and 24.0 nm, respectively, which are consistent with the theoretical lengths of $(PPG)_{10}$ and sequences A, B and C. The length of each Gly-Xaa-Yaa triplet is about 0.9 nm. The lengths of sequences A, B and C are all 81 amino acids, that is, 27 triplets, and the theoretical length is 24.3 nm. The collagen derived from human sequences can also self-assemble to form fibers with periodic bright and dark stripes in this mode. The length of the bright stripes is consistent with the theoretical $(PPG)_{10}$ length, and the dark stripes are 32.6 nm in length, which is consistent with the theoretical length of the sequence H (36 Gly-Xaa-Yaa triplets), proving that the three-segment chimeric design model can form a stable periodic fiber under the drive of N- and C-terminal $(PPG)_{10}$ and is not affected by the sequence replacement of collagen regions.

Example 4 Control of Periodic Length of Fibers by Length of Collagen Region

Figure 6A:
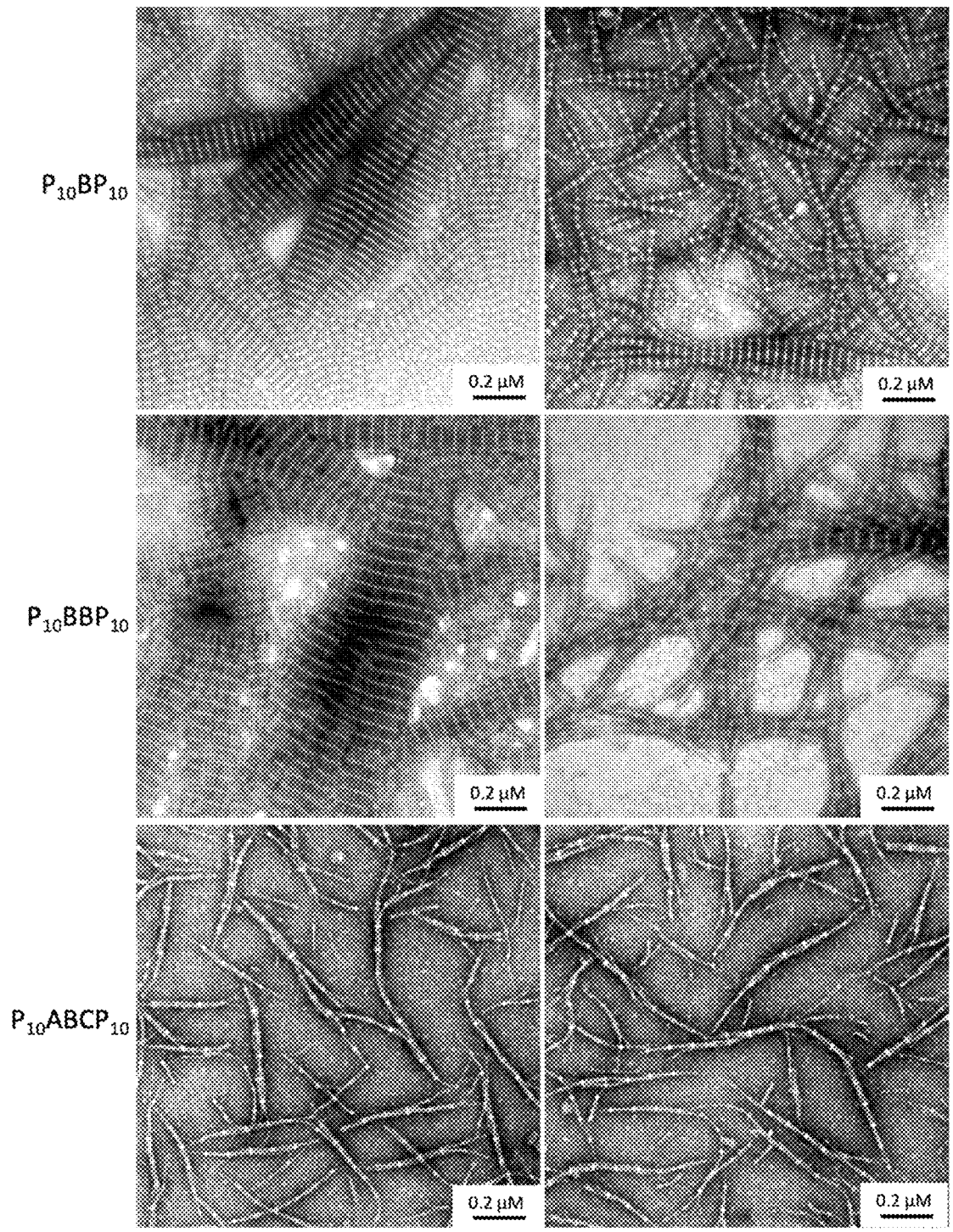
FIG. 6A are transmission electron micrographs of P$_{10}$BP$_{10}$, P$_{10}$BBP$_{10}$ and P$_{10}$ABCP$_{10}$ self-assembled fibers.
Figure 6B:
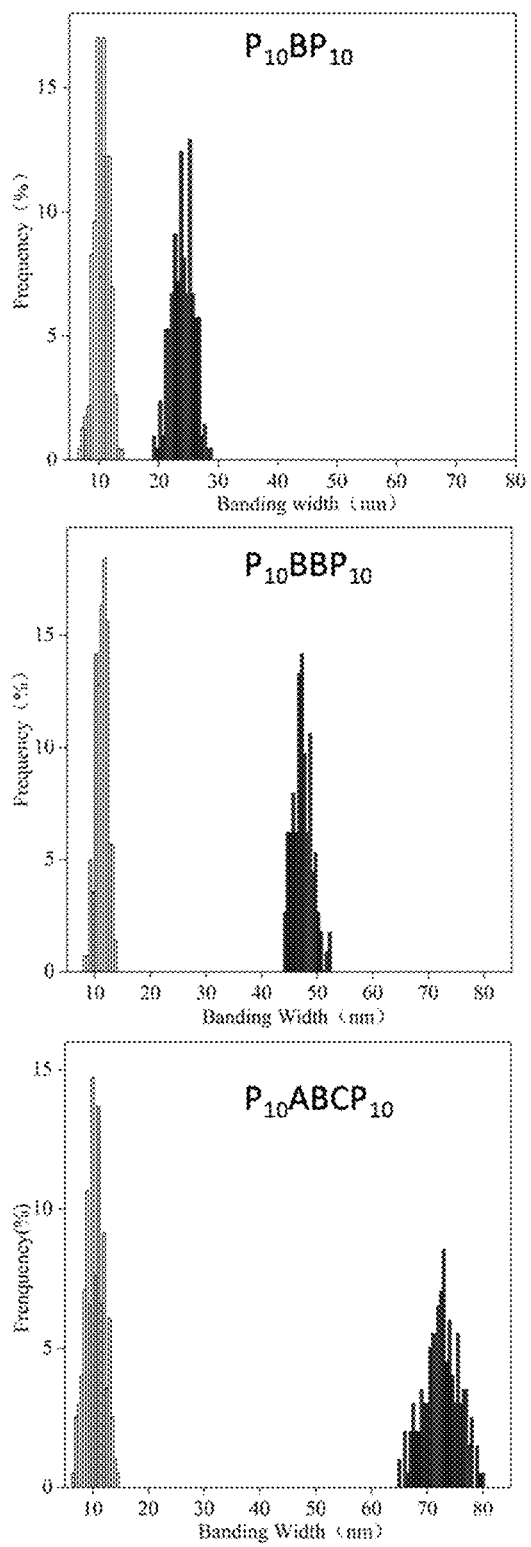
FIG. 6B are statistics of bright and dark stripes in length of the TEM results.

The freeze-dried collagen $P_{10}BP_{10}$, $P_{10}B_2P_{10}$, and $P_{10}ABCP_{10}$ prepared in Example 1 were formulated as a collagen solution according to the method of Example 3, and the fiber morphology was observed. The transmission electron microscope results as shown in FIG. 6A show that the dark stripes of the fibers change with the length of the sequence, which are 24.0 nm, 47.4 nm, and 72.3 nm and are consistent with the theoretical lengths of collagen regions B, 2B, and ABC. The dark stripes of $P_{10}B_2P_{10}$ are about twice that of $P_{10}BP_{10}$, the dark stripes of $P_{10}ABCP_{10}$ are about 3 times that of $P_{10}BP_{10}$, and the length of the bright stripes are all about 10 nm. The results show that the length of the dark stripes of collagen fibers can be controlled by adjusting the length of the collagen region under the three-segment chimeric sequence mode.

Example 5 Verification of Function of Collagen Fibers

The self-assembled fibers in Example 3 were diluted to concentrations of 0.02, 0.04, 0.08, and 0.1 mg/mL. After that, 200 μL of the collagen fiber solution prepared in Example 1, 200 μL of 5% bovine serum albumin (BSA) as a negative control, and 200 μL of 0.04 mg/mL type I collagen as a positive control were added to a 48-well plate, performed in triplicate for each group, allowed to stand at 4° C., and adsorbed for 24 h. After that, the solution was aspirated, 200 μL of DMEM medium containing 5% BSA was added, and allowed to stand at room temperature for 2 h. The mixture was washed 3 times with PBS buffer, then smooth muscle cells were resuspended in DMEM containing 10% FBS at a density of 20,000 cells per well and a cell culture plate is inoculated with 200 μL. After 2 h, the cell suspension was aspirated and the cells were washed with PBS 3 times and then stained with crystal violet. The absorbance was measured at 590 nm and the cell adhesion was observed.

Figure 8A:
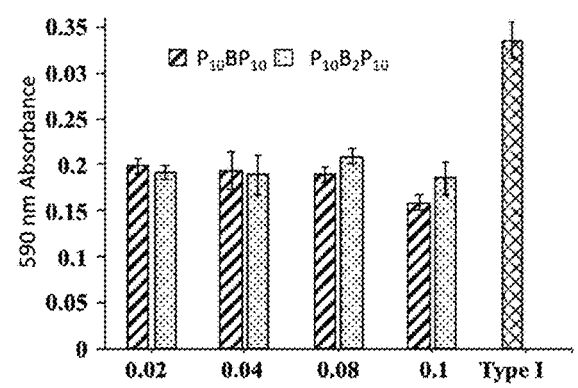
FIG. 8A is the adhesion ability of smooth muscle cells under different collagen concentrations.
Figure 8B:
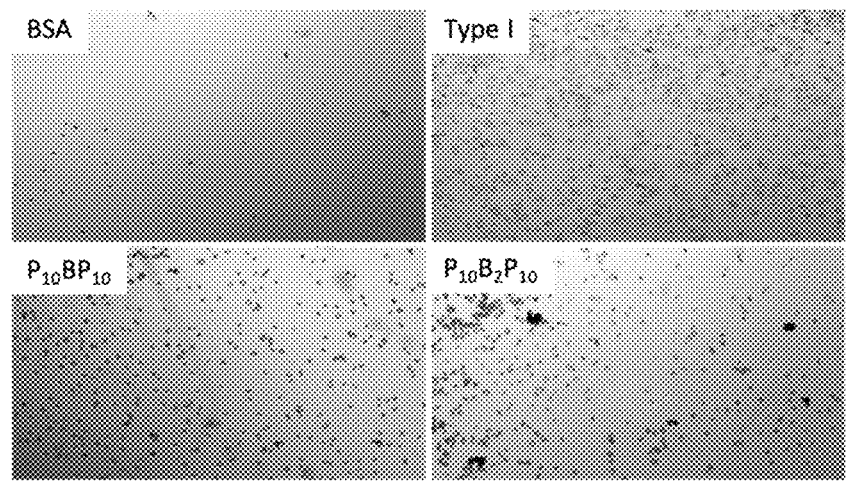
FIG. 8B is the adhesion diagram of smooth muscle cells when the collagen concentration is 0.02 mg/mL.
Figure 8C:
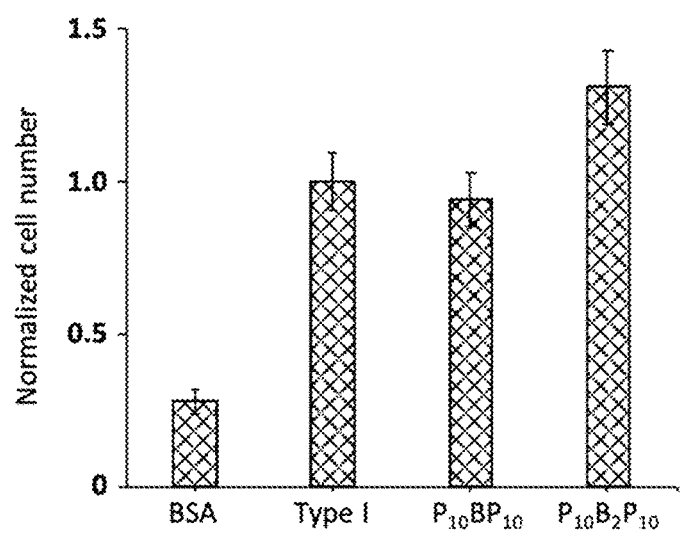
FIG. 8C is the relative percentage of the number of 3T3 mouse fibroblasts growing on the collagen substrate.
Figure 8D:
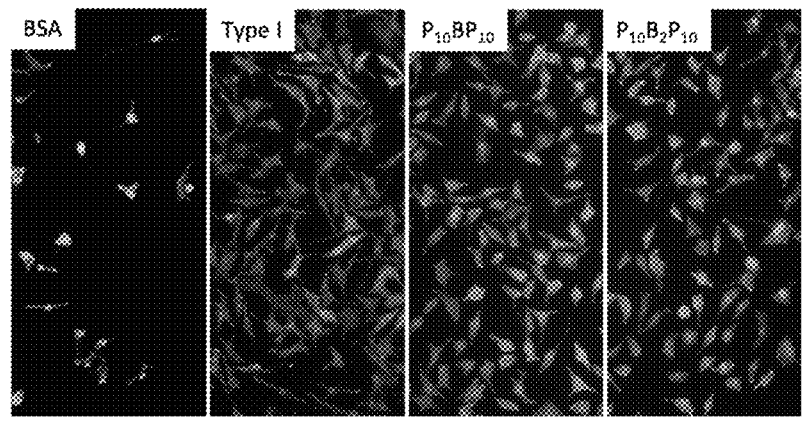
FIG. 8D is the fluorescence staining image of 3T3 mouse fibroblasts growing on the collagen substrate.
Figure 9A:
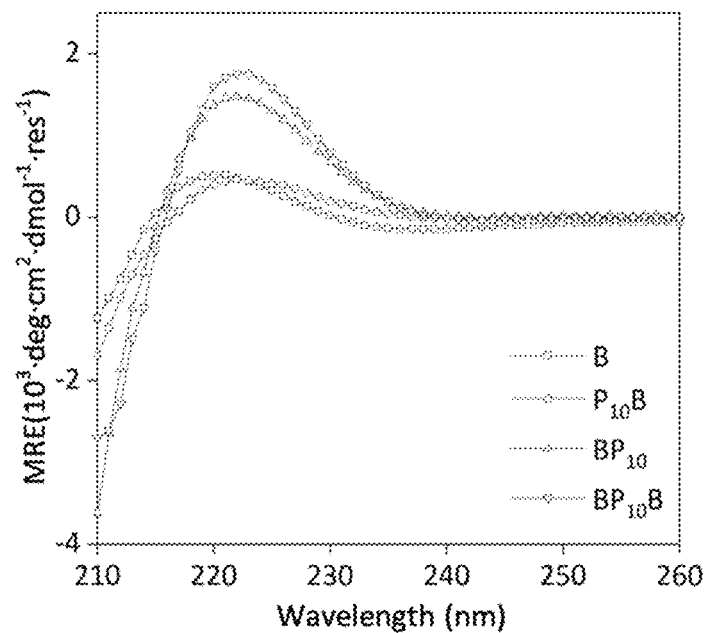
FIG. 9A is the full-wavelength scan spectrum of B, P$_{10}$B, BP$_{10}$ and BP$_{10}$B.
Figure 9B:
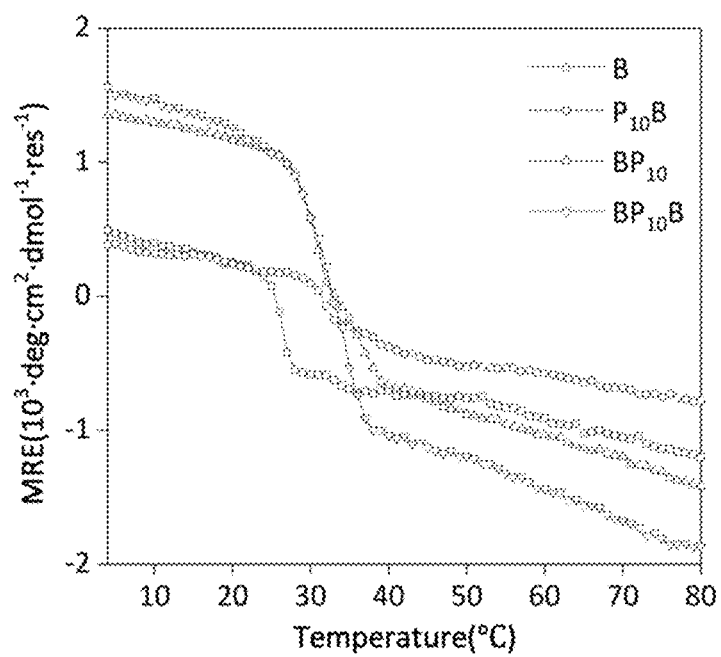
FIG. 9B is the thermo transition curve of the circular dichroism.
Figure 9C:
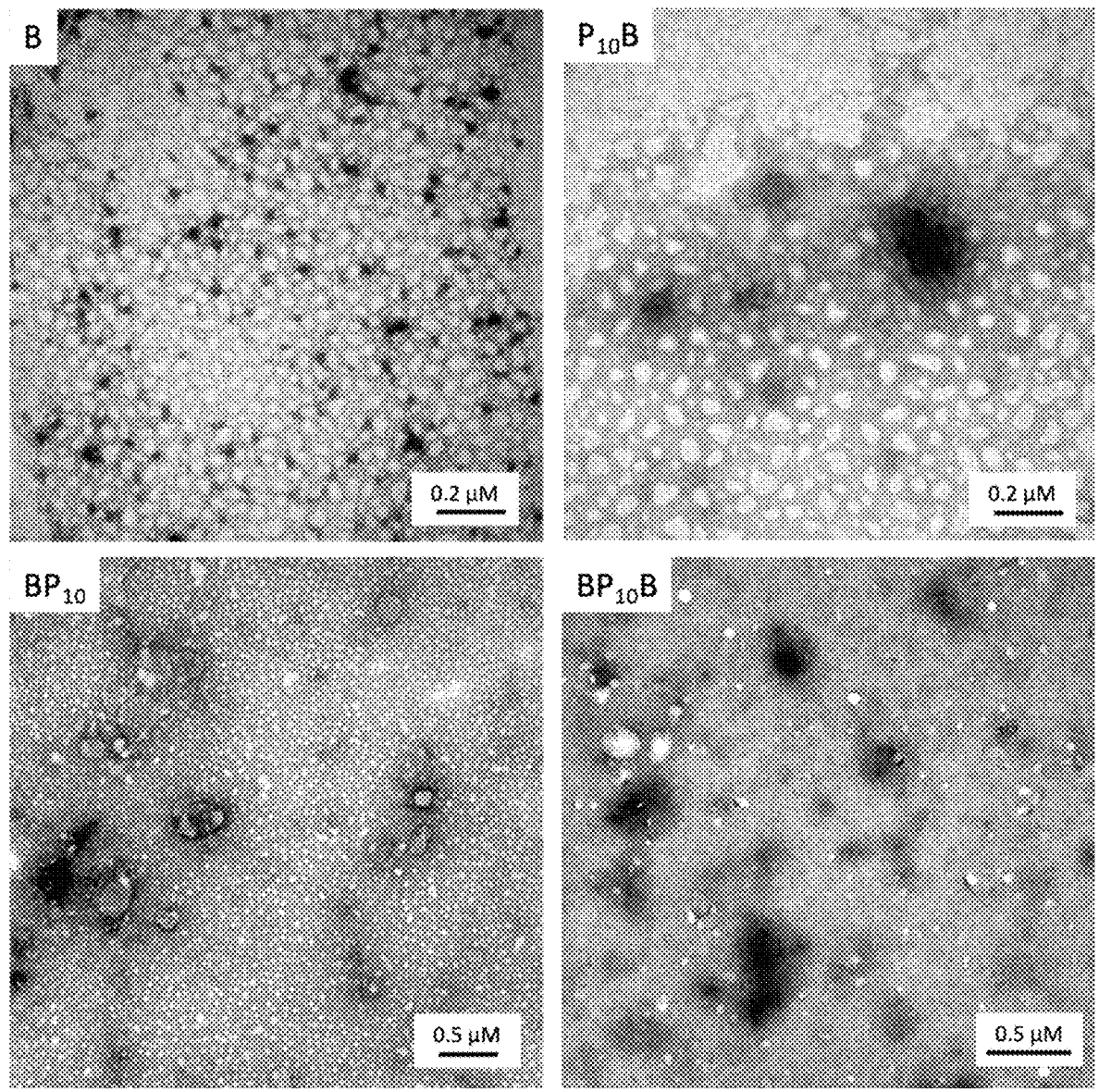
FIG. 9C are transmission electron micrographs of B, P$_{10}$B, BP$_{10}$ and BP$_{10}$B.

As shown in FIG. 8 A and FIGS. 8B, compared with BSA, $P_{10}BP_{10}$ and $P_{10}B_2P_{10}$ can promote cell adhesion very well, and different concentrations have no great effect on cell adhesion. At a concentration of 0.04 mg/mL, their adhesion abilities are about 0.58 times and 0.57 times that of natural type I collagen, respectively.

In the same way, the collagen fibers were adsorbed to a 96-well plate, and then mouse 3T3 cells were resuspended in DMEM containing 4% FBS at a density of 5000 cells per well, and a cell culture plate was inoculated with 100 μL. After culturing for 24 h, the cells were stained with Dapi and phalloidin, the number of cells was counted and the cell morphology was observed. As shown in FIG. 8 C and FIG. 8 D, the adhesion abilities of $P_{10}BP_{10}$ and $P_{10}B_2P_{10}$ to 3T3 cells are comparable to that of natural type I collagen, and are 0.94 times and 1.31 times that of type I collagen. The observation of cell morphology shows that 3T3 cells based on $P_{10}BP_{10}$ and $P_{10}B_2P_{10}$ grow well and have a higher cell extension.

The function of other collagen fibers prepared in Example 1 was verified according to the above method. The results show that the adhesion ability and cell extension of other collagen fibers were equivalent to the effects of $P_{10}BP_{10}$ and $P_{10}B_2P_{10}$.

Comparative Example 1

The specific implementation mode was the same as that in Example 1, except that (PPG)$_{10}$ was replaced with (PPG)$_5$.

```
The amino acid sequence of V-P₅BP₅ (as shown in
SEQ ID NO. 19):
HHHHHHADEQEEKAKVRTELIQELAQGLGGIEKKNFPTLGDEDLDHTYMT

KLLTYLQEREQAENSWRKRLLKGIQDHALDLVPRGSPGPPGPPGPPGPPG

PPGPRGEQGPQGLPGKDGEAGAQGPAGPMGPAGFPGERGEKGEPGTQGAK

GDRGETGPVGPRGERGEAGPAGKDGERGPVGPAGPPGPPGPPGPPGPPG,
and the nucleotide sequence encoding the amino
acid sequence is shown in SEQ ID NO. 20.

The amino acid sequence of V-P₅B₂P₅ (as shown in
SEQ ID NO. 21):
HHHHHHADEQEEKAKVRTELIQELAQGLGGIEKKNFPTLGDEDLDHTYMT

KLLTYLQEREQAENSWRKRLLKGIQDHALDLVPRGSPGPPGPPGPPGPPG

PPGPRGEQGPQGLPGKDGEAGAQGPAGPMGPAGFPGERGEKGEPGTQGAK

GDRGETGPVGPRGERGEAGPAGKDGERGPVGPAGPRGEQGPQGLPGKDGE

AGAQGPAGPMGPAGFPGERGEKGEPGTQGAKGDRGETGPVGPRGERGEAG

PAGKDGERGPVGPAGPPGPPGPPGPPGPPG, and the nucleotide
sequence encoding the amino acid sequence is shown
in SEQ ID NO. 22.
```

Figure 7A:
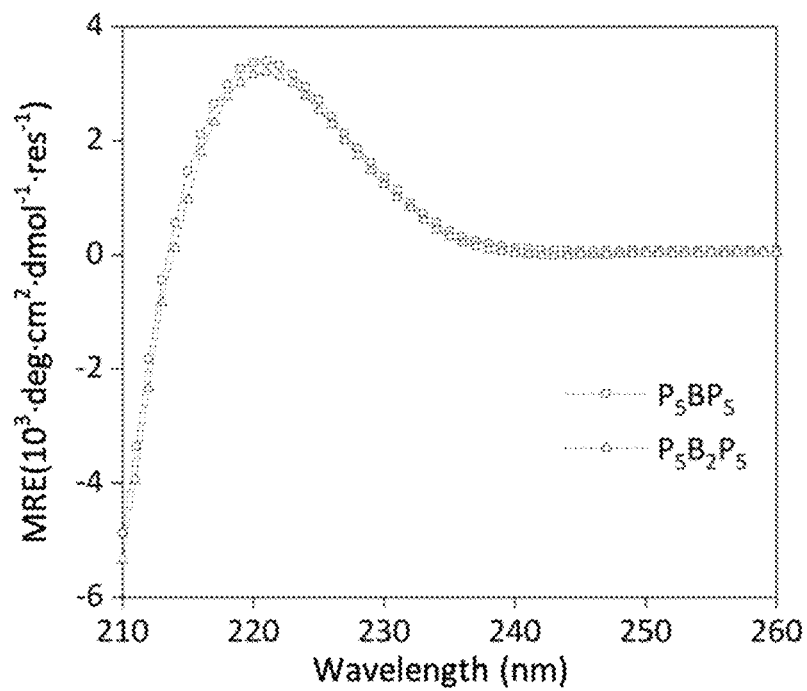
FIG. 7A is the full-wavelength scan spectrum of P$_5$BP$_5$ and P$_5$B$_2$P$_5$.
Figure 7B:
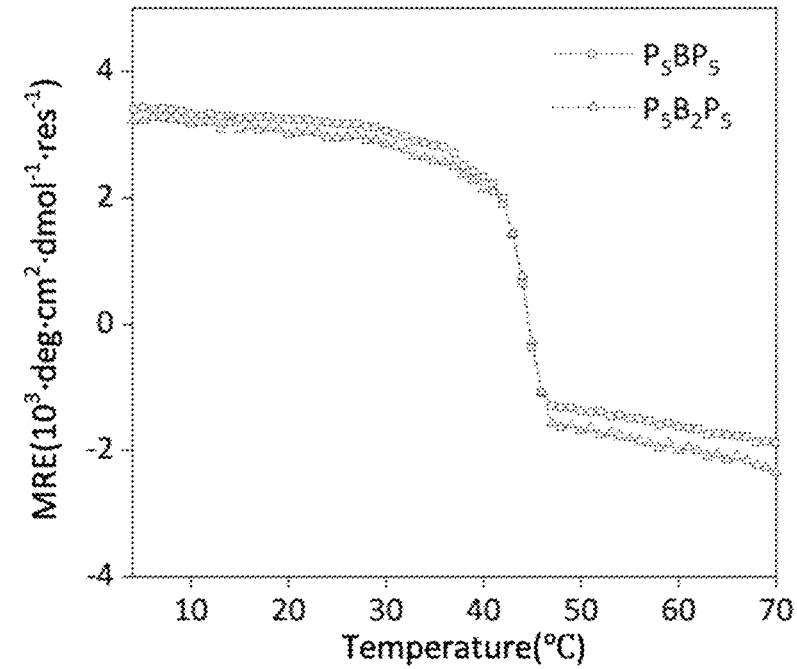
FIG. 7B is thermo transition curve of P$_5$BP$_5$ and P$_5$B$_2$P$_5$.
Figure 7C:
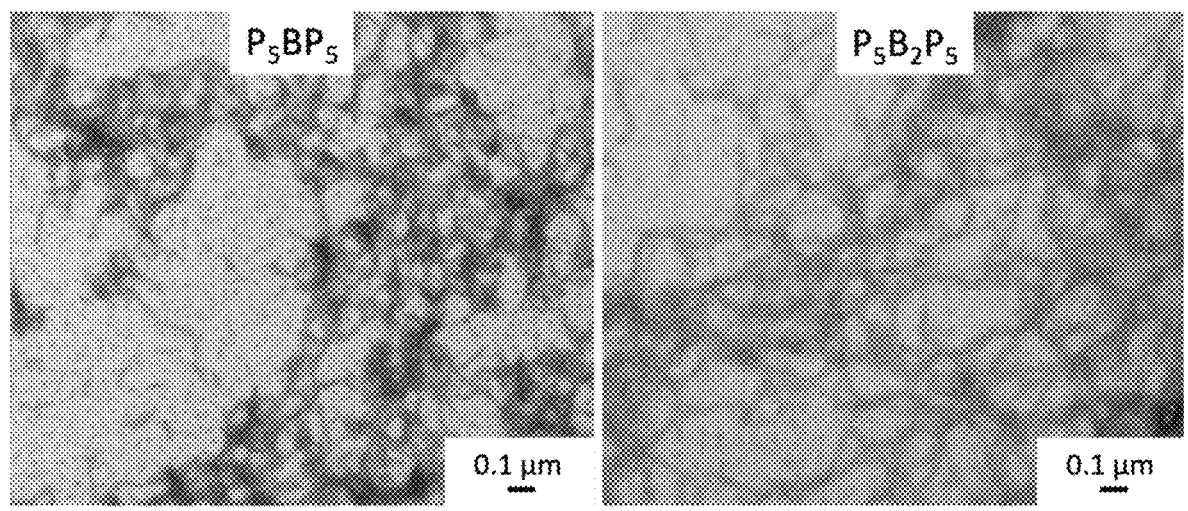
FIG. 7C is the transmission electron micrograph of P$_5$BP$_5$ and P$_5$B$_2$P$_5$ self-assembled fibers.

As shown in FIG. 7A~ FIG. 7 C, the results of full-wavelength scan and thermo transition experiment show that both of the chimeric collagen P$_5$BP$_5$ and P$_5$B$_2$P$_5$ designed in this patent can be folded correctly to form a collagen triple helix structure, and have a high thermal stability, but the transmission electron microscopy results show that although the designed collagen P$_5$BP$_5$ and P$_5$BP$_5$ can self-assemble to form fibers, the fibers do not have periodic bright and dark stripes.

Comparative Example 2

The specific implementation mode was the same as in Example 1, except that (GPP)$_{10}$ was inserted only at the C-terminus, N-terminus, or middle portion of the CL-domain (using the B collagen sequence of Scl2 here), or no (GPP)$_{10}$ was added.

```
(1) The amino acid sequence of V-B (as shown in
SEQ ID NO. 25):
HHHHHHADEQEEKAKVRTELIQELAQGLGGIEKKNFPTLGDEDLDHTYMT

KLLTYLQEREQAENSWRKRLLKGIQDHALDLVPRGSPGPRGEQGPQGLPG

KDGEAGAQGPAGPMGPAGFPGERGEKGEPGTQGAKGDRGETGPVGPRGER

GEAGPAGKDGERGPVGPAG.

The nucleotide sequence encoding V-B (as shown in
SEQ ID NO. 26):
CCATGGGCCATCATCATCATCACCACGCCGATGAACAAGAAGAGAAAGCA

AAGGTGCGCACCGAACTGATTCAAGAACTGGCACAAGGTCTGGGCGGTAT

CGAAAAGAAGAACTTCCCGACTTTAGGTGATGAGGATTTAGATCACACCT

ACATGACCAAACTGCTGACCTATTTACAAGAACGCGAACAAGCTGAAAAT

AGCTGGCGCAAACGTCTGCTGAAAGGCATCCAAGATCATGCACTGGATCT

GGTTCCGCGTGGTAGCCCCGGTCCTCGCGGTGAACAAGGTCCGCAAGGTC
```
```
TGCCGGGTAAAGATGGTGAAGCCGGTGCACAAGGTCCGGCTGGTCCTATG

GGCCCGGCCGGCTTTCCGGGCGAACGTGGTGAAAAAGGCGAACCGGGTAC

CCAAGGTGCCAAAGGTGATCGTGGCGAAACCGGTCCGGTTGGCCCTCGTG

GCGAACGCGGTGAAGCTGGTCCGGCTGGCAAAGACGGTGAACGTGGTCCC

GTTGGTCCGGCCGGTTAAGGATCC.

(2) The amino acid sequence of V-P₁₀B (as shown in
SEQ ID NO. 27):
HHHHHHADEQEEKAKVRTELIQELAQGLGGIEKKNFPTLGDEDLDHTYMT

KLLTYLQEREQAENSWRKRLLKGIQDHALDLVPRGSPGPPGPPGPPGPPG

PPGPPGPPGPPGPPGPRGEQGPQGLPGKDGEAGAQGPAGPMGPAGFP

GERGEKGEPGTQGAKGDRGETGPVGPRGERGEAGPAGKDGERGPVGPAG.

The nucleotide sequence encoding V-P₁₀B (as shown
in SEQ ID NO. 28):
CCATGGGCCATCATCATCATCACCACGCCGATGAGCAAGAAGAAAAGGCC

AAGGTTCGCACCGAACTGATTCAAGAACTGGCCCAAGGTCTGGGTGGCAT

CGAGAAAAAGAACTTCCCGACTTTAGGCGACGAAGATTTAGACCACACCT

ATATGACCAAGCTGCTGACCTATTTACAAGAACGCGAACAAGCTGAAAAC

AGTTGGCGTAAACGTTTACTGAAGGGTATCCAAGATCACGCACTGGATCT

GGTTCCGCGTGGTTCTCCCGGTCCCCCGGCCCCCCGGTCCCCCCGGTC

CCCCCGGTCCTCCCGGCCCCCCGGTCCCCCGGTCCTCCGGGTCCCCCC

GGTCCGCCCGGTCCCCGTGGTGAACAAGGCCCGCAAGGTTTACCGGGCAA

AGACGGTGAAGCTGGTGCACAAGGTCCGGCTGGTCCTATGGGCCCGGCCG

GTTTTCCGGGTGAGCGTGGTGAAAAAGGCGAACCGGGCACACAAGGCGCA

AAAGGTGATCGCGGTGAAACCGGCCCGTTGGCCCTCGTGGCGAACGTGG

CGAAGCTGGTCCGGCCGGCAAAGATGGTGAGCGTGGCCCCGTTGGCCCCG

CTGGCTAAGGATCC.

(3) The amino acid sequence of V-BP₁₀ (as shown in
SEQ ID NO. 29):
HHHHHHADEQEEKAKVRTELIQELAQGLGGIEKKNFPTLGDEDLDHTYMT

KLLTYLQEREQAENSWRKRLLKGIQDHALDLVPRGSPGPRGEQGPQGLPG

KDGEAGAQGPAGPMGPAGFPGERGEKGEPGTQGAKGDRGETGPVGPRGER

GEAGPAGKDGERGPVGPAGPPGPPGPPGPPGPPGPPGPPGPPGPPGPPG.

The nucleotide sequence encoding V-BP₁₀ (as shown
in SEQ ID NO. 30):
CCATGGGCCATCATCATCATCACCACGCCGATGAGCAAGAAGAAAAGGCC

AAGGTTCGCACCGAACTGATTCAAGAACTGGCCCAAGGTCTGGGTGGCAT

CGAGAAAAAGAACTTCCCGACTTTAGGCGACGAAGATTTAGACCACACCT

ATATGACCAAGCTGCTGACCTATTTACAAGAACGCGAACAAGCTGAAAAC

AGTTGGCGTAAACGTTTACTGAAGGGTATCCAAGATCACGCACTGGATCT

GGTTCCGCGTGGTTCTCCCGGTCCGCGTGGCGAACAAGGTCCTCAAGGTT

TACCGGGTAAAGATGGCGAAGCCGGTGCACAAGGTCCCGCTGGTCCTATG

GGTCCCGCTGGTTTTCCCGGTGAACGCGGCGAAAAAGGTGAACCCGGTAC

CCAAGGTGCAAAGGGTGACCGTGGTGAGACCGGTCCCGTTGGCCCTCGTG

GTGAACGTGGTGAAGCCGGTCCGGCTGGTAAAGACGGCGAGCGCGGCCCG
```

```
GTTGGCCCCGCTGGCCCCCCCGGTCCCCCCGGTCCCCCCGGTCCTCCCGG

TCCCCCCGGTCCGCCCGGTCCCCCCGGTCCCCCCGGTCCCCCCGGTCCTC

CGGGCTAAGGATCC.
```

(3) The amino acid sequence of V-BP$_{10}$B (as shown in SEQ ID NO. 31):
```
HHHHHHADEQEEKAKVRTELIQELAQGLGGIEKKNFPTLGDEDLDHTYMT

KLLTYLQEREQAENSWRKRLLKGIQDHALDLVPRGSPGPRGEQGPQGLPG

KDGEAGAQGPAGPMGPAGFPGERGEKGEPGPPGPPGPPGPPGPPGPPGPP

GPPGPPGPPGTQGAKGDRGETGPVGPRGERGEAGPAGKDGERGPVGPAG.
```

The nucleotide sequence encoding V-BP$_{10}$B (as shown in SEQ ID NO. 32):
```
CCATGGGCCATCATCACCATCACCATGCCGATGAGCAAGAAGAAAAAGCC

AAAGTGCGCACCGAACTGATCCAAGAACTGGCACAAGGTCTGGGTGGCAT

CGAGAAGAAAAACTTCCCGACTTTAGGCGATGAAGATTTAGACCACACCT

ACATGACCAAACTGCTGACCTATTTACAAGAACGTGAGCAAGCTGAGAAT

AGCTGGCGCAAGCGTTTACTGAAAGGCATTCAAGATCATGCTTTAGATTT

AGTTCCGCGTGGTAGTCCGGGTCCGCGTGGTGAACAAGGTCCTCAAGGTC

TGCCGGGTAAAGACGGTGAAGCTGGTGCCCAAGGCCCGGCTGGTCCGATG

GGTCCCGCTGGTTTTCCGGGCGAACGTGGTGAAAAAGGTGAACCCGGTCC

CCCGGGTCCTCCCGGTCCGCCGGGCCCGCCCGGTCCCCCCGGTCCGCCCG

GTCCCCCGGGCCCCCCCGGTCCTCCCGGCCCTCCGGGTACCCAAGGTGCC

AAAGGTGATCGTGGTGAAACTGGTCCGGTTGGTCCTCGCGGTGAACGCGG

CGAAGCTGGTCCCGCTGGTAAAGATGGTGAGCGCGGTCCCGTTGGTCCGG

CTGGTTAAGGATCC.
```

As shown in FIG. 8A–D, the results show that the collagen sequences designed in this example can all be folded correctly to form a collagen triple helix structure, but the transmission electron microscope results show that none of the designed collagens can self-assemble to form fibers.

---

What is claimed is:

1. A single-chain protein for expressing a type I-like collagen, wherein:
   the single-chain protein consists of an amino acid sequence as set forth in:

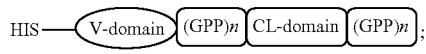

V-domain has an amino acid sequence as set forth in SEQ ID NO:1;
   (GPP)n is (glycine-proline-proline)n;
   n=10;
   the CL-domain has an amino acid sequence as set forth in any sequence of SEQ ID NOS: 2 to 6;
   HIS is a 6×His tag;
   the V-domain and (GPP)$_n$ are ligated by LVPRGSP (SEQ ID NO:33); and
   the single-chain protein self-assembles with additional single-chain proteins to form the type I-like collagen fibers with D-periodic band structure comprising uniform spacing of bright and dark alternating stripes when viewed with electron microscope.

2. The single-chain protein according to claim 1, wherein the bright and dark stripes have a length of p×1 nm, wherein p is an integer greater than 5.

3. A gene encoding the single-chain protein according to claim 1.

4. A plasmid or a cell, wherein the plasmid comprises the gene according to claim 3, and wherein the cell comprises the gene according to claim 3.

5. The plasmid or the cell according to claim 4, wherein the plasmid is a pColdIII series plasmid or a pET series plasmid.

6. The plasmid or the cell according to claim 4, wherein the cell is an *E. coli* cell selected from the group consisting of: *E. coli* BL21, *E. coli* BL21 (DE3), *E. coli* JM109, *E. coli* DH5α, and *E. coli* TOP10.

7. A method for preparing type I collagen-like fiber, comprising the following steps:
   (1) culturing the cell of claim 4 under conditions that induce expression of the gene;
   (2) adding a trypsin to a purified gene product of step (1) and incubating at 20° C. to 25° C. for at least 6 hours to obtain the single-chain protein of the type I-like collagen; and
   (3) adding the single-chain protein of a type I-like collagen obtained in step (2) to a solution at a final concentration of 0.1 mmol/L to 1 mmol/L, and storing the solution at 2° C. to 37° C.

8. The method according to claim 7, wherein the gene in step (1) has a nucleotide sequence as set forth in any one of SEQ ID NOS: 13 to 15, 17, and 18.

9. The method according to claim 7, wherein the storing time in step (3) is 24 hours or more.

10. The method according to claim 7, wherein in step (3), the collagen is added to the solution at a final concentration of 0.5 mmol/L, and storing the solution at 4° C. to 37° C. for at least 2 days.

* * * * *

SEQUENCE LISTING

<160> NUMBER OF SEQ ID NOS: 33

<210> SEQ ID NO 1
<211> LENGTH: 74
<212> TYPE: PRT
<213> ORGANISM: Artificial sequence
<220> FEATURE:
<223> OTHER INFORMATION: Protein translated from synthetic DNA

<400> SEQUENCE: 1

Ala Asp Glu Gln Glu Glu Lys Ala Lys Val Arg Thr Glu Leu Ile Gln
 1               5                  10                  15

Glu Leu Ala Gln Gly Leu Gly Gly Ile Glu Lys Lys Asn Phe Pro Thr
            20                  25                  30

Leu Gly Asp Glu Asp Leu Asp His Thr Tyr Met Thr Lys Leu Leu Thr
        35                  40                  45

Tyr Leu Gln Glu Arg Glu Gln Ala Glu Asn Ser Trp Arg Lys Arg Leu
    50                  55                  60

Leu Lys Gly Ile Gln Asp His Ala Leu Asp
65                  70

<210> SEQ ID NO 2
<211> LENGTH: 81
<212> TYPE: PRT
<213> ORGANISM: Streptococcus pyogenes

<400> SEQUENCE: 2

Gln Asp Gly Arg Asn Gly Glu Arg Gly Glu Gln Gly Pro Thr Gly Pro
 1               5                  10                  15

Thr Gly Pro Ala Gly Pro Arg Gly Leu Gln Gly Leu Gln Gly Phe Pro
            20                  25                  30

Gly Glu Arg Gly Glu Gln Gly Pro Thr Gly Pro Ala Gly Pro Arg Gly
        35                  40                  45

Leu Gln Gly Glu Arg Gly Glu Gln Gly Pro Thr Gly Leu Ala Gly Lys
    50                  55                  60

Ala Gly Glu Ala Gly Ala Lys Gly Glu Thr Gly Pro Ala Gly Pro Gln
65                  70                  75                  80

Gly

<210> SEQ ID NO 3
<211> LENGTH: 81
<212> TYPE: PRT
<213> ORGANISM: Streptococcus pyogenes

<400> SEQUENCE: 3

```
Pro Arg Gly Glu Gln Gly Pro Gln Gly Leu Pro Gly Lys Asp Gly Glu
1               5                   10                  15

Ala Gly Ala Gln Gly Pro Ala Gly Pro Met Gly Pro Ala Gly Phe Pro
            20                  25                  30

Gly Glu Arg Gly Glu Lys Gly Glu Pro Gly Thr Gln Gly Ala Lys Gly
        35                  40                  45

Asp Arg Gly Glu Thr Gly Pro Val Gly Pro Arg Gly Glu Arg Gly Glu
    50                  55                  60

Ala Gly Pro Ala Gly Lys Asp Gly Glu Arg Gly Pro Val Gly Pro Ala
65                  70                  75                  80

Gly
```

<210> SEQ ID NO 4
<211> LENGTH: 78
<212> TYPE: PRT
<213> ORGANISM: Streptococcus pyogenes

<400> SEQUENCE: 4

```
Lys Asp Gly Gln Asn Gly Gln Asp Gly Leu Pro Gly Lys Asp Gly Lys
1               5                   10                  15

Asp Gly Gln Asn Gly Lys Asp Gly Leu Pro Gly Lys Asp Gly Lys Asp
            20                  25                  30

Gly Gln Asn Gly Lys Asp Gly Leu Pro Gly Lys Asp Gly Lys Asp Gly
        35                  40                  45

Gln Asp Gly Lys Asp Gly Leu Pro Gly Lys Asp Gly Lys Asp Gly Leu
    50                  55                  60

Pro Gly Lys Asp Gly Lys Asp Gly Gln Pro Gly Lys Pro Gly
65                  70                  75
```

<210> SEQ ID NO 5
<211> LENGTH: 237
<212> TYPE: PRT
<213> ORGANISM: Streptococcus pyogenes

<400> SEQUENCE: 5

```
Gln Asp Gly Arg Asn Gly Glu Arg Gly Glu Gln Gly Pro Thr Gly Pro
1               5                   10                  15

Thr Gly Pro Ala Gly Pro Arg Gly Leu Gln Gly Leu Gln Gly Leu Gln
            20                  25                  30

Gly Glu Arg Gly Glu Gln Gly Pro Thr Gly Pro Ala Gly Pro Arg Gly
        35                  40                  45

Leu Gln Gly Glu Arg Gly Glu Gln Gly Pro Thr Gly Leu Ala Gly Lys
    50                  55                  60

Ala Gly Glu Ala Gly Ala Lys Gly Glu Thr Gly Pro Ala Gly Pro Gln
65                  70                  75                  80

Gly Pro Arg Gly Glu Gln Gly Pro Gln Gly Leu Pro Gly Lys Asp Gly
            85                  90                  95

Glu Ala Gly Ala Gln Gly Pro Ala Gly Pro Met Gly Pro Ala Gly Glu
            100                 105                 110
```

```
Arg Gly Glu Lys Gly Glu Pro Gly Thr Gln Gly Ala Lys Gly Asp Arg
            115                 120                 125

Gly Glu Thr Gly Pro Val Gly Pro Arg Gly Arg Gly Glu Ala Gly
        130                 135                 140

Pro Ala Gly Lys Asp Gly Glu Arg Gly Pro Val Gly Pro Ala Gly Lys
145                 150                 155                 160

Asp Gly Gln Asn Gly Gln Asp Gly Leu Pro Gly Lys Asp Gly Lys Asp
                165                 170                 175

Gly Gln Asn Gly Lys Asp Gly Leu Pro Gly Lys Asp Gly Lys Asp Gly
            180                 185                 190

Gln Asn Gly Lys Asp Gly Leu Pro Gly Lys Asp Gly Lys Asp Gly Gln
        195                 200                 205

Asp Gly Lys Asp Gly Leu Pro Gly Lys Asp Gly Lys Asp Gly Leu Pro
210                 215                 220

Gly Lys Asp Gly Lys Asp Gly Gln Pro Gly Lys Pro Gly
225                 230                 235

<210> SEQ ID NO 6
<211> LENGTH: 108
<212> TYPE: PRT
<213> ORGANISM: Homo sapiens

<400> SEQUENCE: 6

Gly Glu Arg Gly Pro Pro Gly Pro Gln Gly Ala Arg Gly Leu Pro Gly
1               5                   10                  15

Ala Pro Gly Gln Met Gly Pro Arg Gly Leu Pro Gly Glu Arg Gly Arg
            20                  25                  30

Pro Gly Ala Pro Gly Pro Ala Gly Ala Arg Gly Glu Pro Gly Ala Pro
        35                  40                  45

Gly Ser Lys Gly Asp Thr Gly Ala Lys Gly Glu Pro Gly Pro Val Gly
    50                  55                  60

Val Gln Gly Pro Pro Gly Pro Ala Gly Glu Glu Gly Lys Arg Gly Ala
65                  70                  75                  80

Arg Gly Glu Pro Gly Pro Thr Gly Pro Ala Gly Pro Lys Gly Ser Pro
                85                  90                  95

Gly Glu Ala Gly Arg Pro Gly Glu Ala Gly Leu Pro
            100                 105

<210> SEQ ID NO 7
<211> LENGTH: 229
<212> TYPE: PRT
<213> ORGANISM: Artificial Sequence
<220> FEATURE:
<223> OTHER INFORMATION: Protein translated from synthetic DNA

<400> SEQUENCE: 7

His His His His His His Ala Asp Glu Gln Glu Glu Lys Ala Lys Val
1               5                   10                  15

Arg Thr Glu Leu Ile Gln Glu Leu Ala Gln Gly Leu Gly Gly Ile Glu
            20                  25                  30

Lys Lys Asn Phe Pro Thr Leu Gly Asp Glu Asp Leu Asp His Thr Tyr
        35                  40                  45

Met Thr Lys Leu Leu Thr Tyr Leu Gln Glu Arg Glu Gln Ala Glu Asn
    50                  55                  60

Ser Trp Arg Lys Arg Leu Leu Lys Gly Ile Gln Asp His Ala Leu Asp
65                  70                  75                  80
```

```
Leu Val Pro Arg Gly Ser Pro Gly Pro Pro Gly Pro Pro
            85                  90              95

Gly Pro Pro Gly Pro Pro Gly Pro Pro Gly Pro Pro Gly
            100             105             110

Pro Pro Gly Pro Pro Gly Gln Asp Gly Arg Asn Gly Glu Arg Gly Glu
            115             120             125

Gln Gly Pro Thr Gly Pro Thr Gly Pro Ala Gly Pro Arg Gly Leu Gln
130             135             140

Gly Leu Gln Gly Phe Pro Gly Glu Arg Gly Glu Gln Gly Pro Thr Gly
145             150             155             160

Pro Ala Gly Pro Arg Gly Leu Gln Gly Glu Arg Gly Glu Gln Gly Pro
                165             170             175

Thr Gly Leu Ala Gly Lys Ala Gly Glu Ala Gly Ala Lys Gly Glu Thr
            180             185             190

Gly Pro Ala Gly Pro Gln Gly Pro Pro Gly Pro Pro Gly Pro Pro Gly
            195             200             205

Pro Pro Gly Pro Pro Gly Pro Pro Gly Pro Pro Gly Pro Pro Gly Pro
    210             215             220

Pro Gly Pro Pro Gly
225
```

<210> SEQ ID NO 8
<211> LENGTH: 229
<212> TYPE: PRT
<213> ORGANISM: Artificial Sequence
<220> FEATURE:
<223> OTHER INFORMATION: Protein translated from synthetic DNA

<400> SEQUENCE: 8

```
His His His His His His Ala Asp Glu Gln Glu Glu Lys Ala Lys Val
1               5                   10                  15

Arg Thr Glu Leu Ile Gln Glu Leu Ala Gln Gly Leu Gly Gly Ile Glu
            20                  25                  30

Lys Lys Asn Phe Pro Thr Leu Gly Asp Glu Asp Leu Asp His Thr Tyr
            35                  40                  45

Met Thr Lys Leu Leu Thr Tyr Leu Gln Glu Arg Glu Gln Ala Glu Asn
50              55                  60

Ser Trp Arg Lys Arg Leu Leu Lys Gly Ile Gln Asp His Ala Leu Asp
65                  70                  75                  80

Leu Val Pro Arg Gly Ser Pro Gly Pro Pro Gly Pro Pro Gly Pro Pro
            85                  90                  95

Gly Pro Pro Gly Pro Pro Gly Pro Pro Gly Pro Pro Gly Pro Pro Gly
            100             105             110

Pro Pro Gly Pro Pro Gly Pro Arg Gly Glu Gln Gly Pro Gln Gly Leu
            115             120             125

Pro Gly Lys Asp Gly Glu Ala Gly Ala Gln Gly Pro Ala Gly Pro Met
130             135             140

Gly Pro Ala Gly Phe Pro Gly Glu Arg Gly Glu Lys Gly Glu Pro Gly
145             150             155             160

Thr Gln Gly Ala Lys Gly Asp Arg Gly Glu Thr Gly Pro Val Gly Pro
                165             170             175

Arg Gly Glu Arg Gly Glu Ala Gly Pro Ala Gly Lys Asp Gly Glu Arg
            180             185             190

Gly Pro Val Gly Pro Ala Gly Pro Pro Gly Pro Pro Gly Pro Pro Gly
            195             200             205
```

Pro Pro Gly Pro Pro Gly Pro Pro Gly Pro Pro Gly Pro
        210                 215                 220

Pro Gly Pro Pro Gly
225

<210> SEQ ID NO 9
<211> LENGTH: 226
<212> TYPE: PRT
<213> ORGANISM: Artificial Sequence
<220> FEATURE:
<223> OTHER INFORMATION: Protein translated from synthetic DNA

<400> SEQUENCE: 9

His His His His His His Ala Asp Glu Gln Glu Glu Lys Ala Lys Val
1               5                   10                  15

Arg Thr Glu Leu Ile Gln Glu Leu Ala Gln Gly Leu Gly Gly Ile Glu
            20                  25                  30

Lys Lys Asn Phe Pro Thr Leu Gly Asp Glu Asp Leu Asp His Thr Tyr
        35                  40                  45

Met Thr Lys Leu Leu Thr Tyr Leu Gln Glu Arg Glu Gln Ala Glu Asn
    50                  55                  60

Ser Trp Arg Lys Arg Leu Leu Lys Gly Ile Gln Asp His Ala Leu Asp
65                  70                  75                  80

Leu Val Pro Arg Gly Ser Pro Gly Pro Pro Gly Pro Pro Gly Pro Pro
                85                  90                  95

Gly Pro Pro Gly Pro Pro Gly Pro Pro Gly Pro Pro Gly Pro Pro Gly
                100                 105                 110

Pro Pro Gly Pro Pro Gly Lys Asp Gly Gln Asn Gly Gln Asp Gly Leu
            115                 120                 125

Pro Gly Lys Asp Gly Lys Asp Gly Gln Asn Gly Lys Asp Gly Leu Pro
    130                 135                 140

Gly Lys Asp Gly Lys Asp Gly Gln Asn Gly Lys Asp Gly Leu Pro Gly
145                 150                 155                 160

Lys Asp Gly Lys Asp Gly Gln Asp Gly Lys Asp Gly Leu Pro Gly Lys
                165                 170                 175

Asp Gly Lys Asp Gly Leu Pro Gly Lys Asp Gly Lys Asp Gly Gln Pro
            180                 185                 190

Gly Lys Pro Gly Pro Gly Pro Gly Pro Gly Pro Pro Gly Pro Pro Gly
        195                 200                 205

Pro Pro Gly Pro Pro Gly Pro Pro Gly Pro Pro Gly Pro Pro Gly Pro
    210                 215                 220

Pro Gly
225

<210> SEQ ID NO 10
<211> LENGTH: 310
<212> TYPE: PRT
<213> ORGANISM: Artificial Sequence
<220> FEATURE:
<223> OTHER INFORMATION: Protein translated from synthetic DNA

<400> SEQUENCE: 10

His His His His His His Ala Asp Glu Gln Glu Glu Lys Ala Lys Val
1               5                   10                  15

Arg Thr Glu Leu Ile Gln Glu Leu Ala Gln Gly Leu Gly Gly Ile Glu
            20                  25                  30

```
Lys Lys Asn Phe Pro Thr Leu Gly Asp Glu Asp Leu Asp His Thr Tyr
            35                  40                  45
Met Thr Lys Leu Leu Thr Tyr Leu Gln Glu Arg Glu Gln Ala Glu Asn
 50                  55                  60
Ser Trp Arg Lys Arg Leu Leu Lys Gly Ile Gln Asp His Ala Leu Asp
 65                  70                  75                  80
Leu Val Pro Arg Gly Ser Pro Gly Pro Pro Gly Pro Pro
                85                  90                  95
Gly Pro Pro Gly Pro Pro Gly Pro Pro Gly Pro Pro Gly
                100                 105                 110
Pro Pro Gly Pro Pro Gly Pro Arg Gly Glu Gln Gly Pro Gln Gly Leu
                115                 120                 125
Pro Gly Lys Asp Gly Glu Ala Gly Ala Gln Gly Pro Ala Gly Pro Met
            130                 135                 140
Gly Pro Ala Gly Phe Pro Gly Glu Arg Gly Glu Lys Gly Glu Pro Gly
145                 150                 155                 160
Thr Gln Gly Ala Lys Gly Asp Arg Gly Glu Thr Gly Pro Val Gly Pro
                165                 170                 175
Arg Gly Glu Arg Gly Glu Ala Gly Pro Ala Gly Lys Asp Gly Glu Arg
            180                 185                 190
Gly Pro Val Gly Pro Ala Gly Pro Arg Gly Glu Gln Gly Pro Gln Gly
                195                 200                 205
Leu Pro Gly Lys Asp Gly Glu Ala Gly Ala Gln Gly Pro Ala Gly Pro
            210                 215                 220
Met Gly Pro Ala Gly Phe Pro Gly Glu Arg Gly Glu Lys Gly Glu Pro
225                 230                 235                 240
Gly Thr Gln Gly Ala Lys Gly Asp Arg Gly Glu Thr Gly Pro Val Gly
                245                 250                 255
Pro Arg Gly Glu Arg Gly Glu Ala Gly Pro Ala Gly Lys Asp Gly Glu
            260                 265                 270
Arg Gly Pro Val Gly Pro Ala Gly Pro Pro Gly Pro Pro Gly Pro Pro
                275                 280                 285
Gly Pro Pro Gly Pro Pro Gly Pro Pro Gly Pro Pro Gly Pro Pro Gly
            290                 295                 300
Pro Pro Gly Pro Pro Gly
305                 310

<210> SEQ ID NO 11
<211> LENGTH: 385
<212> TYPE: PRT
<213> ORGANISM: Artificial Sequence
<220> FEATURE:
<223> OTHER INFORMATION: Protein translated from synthetic DNA

<400> SEQUENCE: 11

His His His His His Ala Asp Glu Gln Glu Glu Lys Ala Lys Val
 1               5                  10                  15
Arg Thr Glu Leu Ile Gln Glu Leu Ala Gln Gly Leu Gly Gly Ile Glu
                20                  25                  30
Lys Lys Asn Phe Pro Thr Leu Gly Asp Glu Asp Leu Asp His Thr Tyr
            35                  40                  45
Met Thr Lys Leu Leu Thr Tyr Leu Gln Glu Arg Glu Gln Ala Glu Asn
 50                  55                  60
Ser Trp Arg Lys Arg Leu Leu Lys Gly Ile Gln Asp His Ala Leu Asp
 65                  70                  75                  80
```

```
Leu Val Pro Arg Gly Ser Gly Pro Pro Gly Pro Gly Pro Pro
                85                  90                  95

Gly Pro Pro Gly Pro Gly Pro Pro Gly Pro Pro Gly Pro Gly
            100                 105                 110

Pro Pro Gly Pro Pro Gly Gln Asp Gly Arg Asn Gly Glu Arg Gly Glu
        115                 120                 125

Gln Gly Pro Thr Gly Pro Thr Gly Pro Ala Gly Pro Arg Gly Leu Gln
130                 135                 140

Gly Leu Gln Gly Leu Gln Gly Glu Arg Gly Glu Gln Gly Pro Thr Gly
145                 150                 155                 160

Pro Ala Gly Pro Arg Gly Leu Gln Gly Glu Arg Gly Glu Gln Gly Pro
                165                 170                 175

Thr Gly Leu Ala Gly Lys Ala Gly Glu Ala Gly Ala Lys Gly Glu Thr
            180                 185                 190

Gly Pro Ala Gly Pro Gln Gly Pro Arg Gly Glu Gln Gly Pro Gln Gly
            195                 200                 205

Leu Pro Gly Lys Asp Gly Glu Ala Gly Ala Gln Gly Pro Ala Gly Pro
    210                 215                 220

Met Gly Pro Ala Gly Glu Arg Gly Glu Lys Gly Glu Pro Gly Thr Gln
225                 230                 235                 240

Gly Ala Lys Gly Asp Arg Gly Glu Thr Gly Pro Val Gly Pro Arg Gly
                245                 250                 255

Glu Arg Gly Glu Ala Gly Pro Ala Gly Lys Asp Gly Glu Arg Gly Pro
                260                 265                 270

Val Gly Pro Ala Gly Lys Asp Gly Gln Asn Gly Gln Asp Gly Leu Pro
                275                 280                 285

Gly Lys Asp Gly Lys Asp Gly Gln Asn Gly Lys Asp Gly Leu Pro Gly
                290                 295                 300

Lys Asp Gly Lys Asp Gly Gln Asn Gly Lys Asp Gly Leu Pro Gly Lys
305                 310                 315                 320

Asp Gly Lys Asp Gly Gln Asp Gly Lys Asp Gly Leu Pro Gly Lys Asp
                325                 330                 335

Gly Lys Asp Gly Leu Pro Gly Lys Asp Gly Lys Asp Gly Gln Pro Gly
                340                 345                 350

Lys Pro Gly Pro Pro Gly Pro Pro Gly Pro Pro Gly Pro Pro Gly Pro
                355                 360                 365

Pro Gly Pro Pro Gly Pro Pro Gly Pro Pro Gly Pro Pro Gly Pro Pro
            370                 375                 380

Gly
385

<210> SEQ ID NO 12
<211> LENGTH: 256
<212> TYPE: PRT
<213> ORGANISM: Artificial Sequence
<220> FEATURE:
<223> OTHER INFORMATION: Protein translated from synthetic DNA

<400> SEQUENCE: 12

His His His His His His Ala Asp Glu Gln Glu Glu Lys Ala Lys Val
1               5                   10                  15

Arg Thr Glu Leu Ile Gln Glu Leu Ala Gln Gly Leu Gly Gly Ile Glu
            20                  25                  30

Lys Lys Asn Phe Pro Thr Leu Gly Asp Glu Asp Leu Asp His Thr Tyr
        35                  40                  45
```

Met Thr Lys Leu Leu Thr Tyr Leu Gln Glu Arg Glu Gln Ala Glu Asn
50                  55                  60

Ser Trp Arg Lys Arg Leu Lys Gly Ile Gln Asp His Ala Leu Asp
65                  70                  75                  80

Leu Val Pro Arg Gly Ser Pro Gly Pro Pro Gly Pro Pro
                85                  90                  95

Gly Pro Pro Gly Pro Pro Gly Pro Pro Gly Pro Pro Gly
            100                 105                 110

Pro Pro Gly Pro Pro Gly Glu Arg Gly Pro Pro Gly Pro Gln Gly Ala
            115                 120                 125

Arg Gly Leu Pro Gly Ala Pro Gly Gln Met Gly Pro Arg Gly Leu Pro
    130                 135                 140

Gly Glu Arg Gly Arg Pro Gly Ala Pro Gly Pro Ala Gly Ala Arg Gly
145                 150                 155                 160

Glu Pro Gly Ala Pro Gly Ser Lys Gly Asp Thr Gly Ala Lys Gly Glu
                165                 170                 175

Pro Gly Pro Val Gly Val Gln Gly Pro Pro Gly Pro Ala Gly Glu Glu
            180                 185                 190

Gly Lys Arg Gly Ala Arg Gly Glu Pro Gly Pro Thr Gly Pro Ala Gly
    195                 200                 205

Pro Lys Gly Ser Pro Gly Glu Ala Gly Arg Pro Gly Glu Ala Gly Leu
    210                 215                 220

Pro Gly Pro Pro Gly Pro Gly Pro Pro Gly Pro Pro Gly Pro Pro
225                 230                 235                 240

Gly Pro Pro Gly Pro Pro Gly Pro Pro Gly Pro Pro Gly Pro Pro Gly
                245                 250                 255

<210> SEQ ID NO 13
<211> LENGTH: 704
<212> TYPE: DNA
<213> ORGANISM: Artificial Sequence
<220> FEATURE:
<223> OTHER INFORMATION: Synthetic DNA

<400> SEQUENCE: 13

```
ccatgggcca ccaccatcac caccacgccg atgaacaaga agaaaaggcg aaggtgcgca    60
cggaactgat tcaagaactg gcccaaggtc tgggcggcat tgagaagaag aactttccga   120
cgctgggtga cgaagacctc gatcacacct acatgaccaa gctgctgacg tatctccaag   180
aacgcgaaca gccgagaat agctggcgta acgtctgct caaaggcatc caagatcacg   240
cgctggatct ggtgccacgt ggtagtccgg gtccaccggg cccaccgggt ccaccgggcc   300
cgccgggccc gccgggcccg ccgggccac cgggcccgcc gggcccgccg ggcccaccgg   360
gccaagatgg tcgcaatggt gagcgtggtg aacaaggtcc gacgggtccg accggtccag   420
ccggtccgcg tggtctgcaa ggtctgcaag gcttcccggg cgaacgtggc gaacaaggcc   480
cgacgggtcc agccggccca cgtggtctgc aaggtgaacg cggcgaacaa ggtccaaccg   540
gtctggcggg taaagcgggt gaagccggtg cgaaaggtga acgggcccca gcgggtccac   600
aaggcccgcc gggcccaccg gtccaccgg gtccaccggg cccaccgggc cgccgggcc   660
cgccgggccc gccgggcccg ccgggcccgc cgggctaagg atcc                   704
```

<210> SEQ ID NO 14
<211> LENGTH: 704
<212> TYPE: DNA
<213> ORGANISM: Artificial Sequence

```
<220> FEATURE:
<223> OTHER INFORMATION: Synthetic DNA

<400> SEQUENCE: 14
ccatgggcca tcaccaccat catcacgccg atgaacaaga agagaaagcc aaagtgcgca        60
ccgaactgat tcaagaactg gcccaaggtc tgggtggcat tgagaagaag aactttccga       120
cgctgggcga cgaagatctg gaccacacgt acatgaccaa gctgctgacc tatctgcaag       180
aacgcgaaca agccgaaaac agttggcgca acgtctgct gaaaggcatc caagatcacg        240
cgctggatct cgttccacgt ggtagtccgg gtccaccggg cccaccgggt ccaccgggcc       300
caccgggccc accgggccca ccgggcccgc cgggcccgcc gggcccaccg ggcccaccgg       360
gtccacgcgg tgaacaaggc cgcaaggtc tgccgggcaa agatggtgag gcgggtgcgc        420
aaggtccagc cggtccaatg ggtccagccg gtttcccggg cgaacgcggt gaaaaaggcg       480
aaccgggtac gcaaggcgcc aaaggtgatc gcggtgaaac gggtccagtt ggcccgcgtg       540
gtgaacgtgg tgaagcgggt ccggccggta agacggtga acgcgccca gttggtccgg        600 ccggcccacc gggcccaccg ggcccaccgg gcccacccgg cccgccgggc cgccgggcc        660 cgccgggtcc gccgggtcca ccgggcccac cgggctaagg atcc                       704

<210> SEQ ID NO 15
<211> LENGTH: 695
<212> TYPE: DNA
<213> ORGANISM: Artificial Sequence
<220> FEATURE:
<223> OTHER INFORMATION: Synthetic DNA

<400> SEQUENCE: 15
ccatgggcca ccatcatcac catcacgcgg atgagcaaga agagaaagcg aaagtgcgca        60
cggagctgat ccaagaactg gcgcaaggcc tcggcggtat cgagaagaag aacttcccga       120
cgctgggtga tgaggatctg gaccacacgt acatgaccaa actgctcacc tatctgcaag       180
aacgcgaaca agccgaaaac agctggcgca agcgtctgct gaaaggcatt caagatcacg       240
ccctcgatct ggttccgcgc ggtagtccgg gcccaccggg cccgccggc cgccgggcc         300 caccgggccc gccgggccca ccgggtccac cgggcccgcc gggcccaccg ggcccgccgg       360
gcaaagatgg tcagaatggt caagatggtc tcccgggtaa agatggcaaa gacggtcaaa       420
acggtaaaga cggtctgccg ggcaaggatg gtaaggatgg tcagaacggc aaggacggtc       480
tgccgggcaa agatggtaaa gacggccaag atggtaagga cggtctcccg ggtaaggatg       540
gcaaagatgg tctgccgggc aaggacggca agatggcca accgggcaaa ccgggcccac        600
cgggcccgcc gggtccaccg ggtccgccgg gcccgccggg tccaccgggc ccaccgggcc       660 cgccgggcc accgggtccg ccgggctaag gatcc                                  695

<210> SEQ ID NO 16
<211> LENGTH: 947
<212> TYPE: DNA
<213> ORGANISM: Artificial Sequence
<220> FEATURE:
<223> OTHER INFORMATION: Synthetic DNA

<400> SEQUENCE: 16
ccatgggcca tcaccaccat catcacgccg atgaacaaga agagaaagcc aaagtgcgca        60
ccgaactgat tcaagaactg gcccaaggtc tgggtggcat tgagaagaag aactttccga       120
cgctgggcga cgaagatctg gaccacacgt acatgaccaa gctgctgacc tatctgcaag       180
```

-continued

| | |
|---|---|
| aacgcgaaca agccgaaaac agttggcgca aacgtctgct gaaaggcatc caagatcacg | 240 |
| cgctggatct cgttccacgt ggtagtccgg gtccaccggg cccaccgggt ccaccgggcc | 300 |
| caccgggccc accgggccca ccgggcccgc cgggcccgcc gggcccaccg ggcccaccgg | 360 |
| gtccacgcgg tgaacaaggc ccgcaaggtc tgccgggcaa agatggtgag gcgggtgcgc | 420 |
| aaggtccagc cggtccaatg ggtccagccg gtttcccggg cgaacgcggt gaaaaggcg | 480 |
| aaccgggtac gcaaggcgcc aaaggtgatc gcggtgaaac gggtccagtt ggcccgcgtg | 540 |
| gtgaacgtgg tgaagcgggt ccggccggta agacggtga acgcggccca gttggtccgg | 600 |
| ccggcccacg cggtgaacaa ggcccgcaag gtctgccggg caagatggt gaggcgggtg | 660 |
| cgcaaggtcc agccggtcca atgggtccag ccggtttccc gggcgaacgc ggtgaaaaag | 720 |
| gcgaaccggg tacgcaaggc gccaaaggtg atcgcggtga acgggtccca gttggcccgc | 780 |
| gtggtgaacg tggtgaagcg ggtccggccg gtaaagacgg tgaacgcggc ccagttggtc | 840 |
| cggccggccc accgggccca ccgggcccac cgggcccacc gggcccgccg ggcccgccgg | 900 |
| gcccgccggg tccgccgggt ccaccggggcc caccgggcta aggatcc | 947 |

<210> SEQ ID NO 17
<211> LENGTH: 1172
<212> TYPE: DNA
<213> ORGANISM: Artificial Sequence
<220> FEATURE:
<223> OTHER INFORMATION: Synthetic DNA

<400> SEQUENCE: 17

| | |
|---|---|
| ccatgggcca ccaccatcat catcacgcgg acgagcaaga agagaaagcc aaagttcgca | 60 |
| ccgagctgat tcaagaactg gcgcaaggcc tcggcggtat cgagaagaag aactttccga | 120 |
| cgctgggcga tgaggatctg gaccatacgt acatgacgaa gctgctgacc tatctgcaag | 180 |
| aacgcgaaca agcggaaaac agctggcgca agcgcctcct caaaggcatc caagatcatg | 240 |
| ccctcgatct ggttccgcgt ggtagcccgg gcccgccggg cccgccggc ccaccgggcc | 300 |
| cgccgggccc accgggtccg ccgggtccgc cgggcccgcc gggcccaccg ggcccgccgg | 360 |
| gccaagatgg ccgtaacggc gaacgtggtg agcaaggccc aacggcccg acgggtccgg | 420 |
| cgggtccacg tggtctccaa ggtctccaag gtctgcaagg cgaacgcggt gaacaaggtc | 480 |
| cgaccggtcc ggccggtccg cgtggcctcc aaggcgaacg cggcgaacaa ggcccaaccg | 540 |
| gtctggcggg caaagcgggc gaggcgggtg cgaaaggtga accggccca gcgggtccac | 600 |
| aaggtccgcg tggtgaacaa ggcccgcaag gtctgccggg caaggatggc gaagcgggcg | 660 |
| cgcaaggtcc ggccggcccg atgggtccag cgggcgagcg cggtgaaaaa ggcttcccgg | 720 |
| gcgagcgtgg cgccaaaggc gatcgcgcg aaacgggtcc agttggtcca cgcggtgaac | 780 |
| gcggcgaagc cggtccagcc ggtaaagatg gcgaacgtgg tccagttggc ccagccggta | 840 |
| aggatggtca gaatggtcaa gatggcctcc cgggcaagga cggtaaggat ggtcagaatg | 900 |
| gtaaagacgg tctgccgggc aaagatggca aggatggcca gaacggcaaa gatggtctcc | 960 |
| cgggtaagga cggcaaagac ggccaagatg gcaaagacgg cctcccgggc aaggatggca | 1020 |
| aggacggtct cccgggtaaa gacggtaagg atggtcagcc gggcaaaccg ggtccaccgg | 1080 |
| gcccgccggg tccgccgggt ccaccggggcc caccgggccc gccgggccca ccgggcccac | 1140 |
| cgggtccacc gggcccaccg ggctaaggat cc | 1172 |

<210> SEQ ID NO 18
<211> LENGTH: 785

<212> TYPE: DNA
<213> ORGANISM: Artificial Sequence
<220> FEATURE:
<223> OTHER INFORMATION: Synthetic DNA

<400> SEQUENCE: 18

```
ccatgggcca tcatcaccat caccacgccg acgaacaaga agagaaagcc aaggttcgca      60
ccgaactgat tcaagaactg gcgcaaggtc tgggcggcat cgagaaaaaa aacttcccga     120
ccctcggcga tgaggacctc gatcacacgt acatgacgaa actgctgacg tatctgcaag     180
aacgtgaaca agccgaaaac agctggcgca aacgtctgct gaaaggcatc caagatcacg     240
cgctggatct cgtgccacgc ggtagtccgg gcccgccggg cccaccgggc ccaccgggcc     300
caccgggccc gccgggcccg ccgggtccac cgggcccacc gggtccgccg ggcccgccgg     360
gtgagcgtgg tccgccgggc ccacaaggcg cgcgcggtct gccgggcgcg ccgggccaaa     420
tgggtccacg tggtctgccg ggtgaacgtg gccgtccggg cgcgccgggc ccagcgggcg     480
cccgtggtga accgggtgcc ccgggcagca aaggcgatac gggtgccaaa ggcgaaccgg     540
gcccggttgg cgttcaaggc ccaccgggcc cagccggtga agaaggtaaa cgcggcgccc     600
gcggtgaacc gggcccaacg gtccagcgg gcccaaaagg tagcccgggc gaagcgggtc     660
gtccgggcga agccggtctg ccgggcccgc cgggcccgcc gggtccaccg gcccgccgg     720
gcccaccggg cccaccgggc ccgccgggcc caccgggccc accgggccca ccgggctaag     780
gatcc                                                                785
```

<210> SEQ ID NO 19
<211> LENGTH: 199
<212> TYPE: PRT
<213> ORGANISM: Artificial Sequence
<220> FEATURE:
<223> OTHER INFORMATION: Protein translated from synthetic DNA

<400> SEQUENCE: 19

```
His His His His His His Ala Asp Glu Gln Glu Glu Lys Ala Lys Val
1               5                   10                  15
Arg Thr Glu Leu Ile Gln Glu Leu Ala Gln Gly Leu Gly Gly Ile Glu
            20                  25                  30
Lys Lys Asn Phe Pro Thr Leu Gly Asp Glu Asp Leu Asp His Thr Tyr
        35                  40                  45
Met Thr Lys Leu Leu Thr Tyr Leu Gln Glu Arg Glu Gln Ala Glu Asn
    50                  55                  60
Ser Trp Arg Lys Arg Leu Leu Lys Gly Ile Gln Asp His Ala Leu Asp
65                  70                  75                  80
Leu Val Pro Arg Gly Ser Pro Gly Pro Pro Gly Pro Pro Gly Pro Pro
                85                  90                  95
Gly Pro Pro Gly Pro Pro Gly Pro Arg Gly Glu Gln Gly Pro Gln Gly
                100                 105                 110
Leu Pro Gly Lys Asp Gly Glu Ala Gly Ala Gln Gly Pro Ala Gly Pro
            115                 120                 125
Met Gly Pro Ala Gly Phe Pro Gly Glu Arg Gly Glu Lys Gly Glu Pro
        130                 135                 140
Gly Thr Gln Gly Ala Lys Gly Asp Arg Gly Glu Thr Gly Pro Val Gly
145                 150                 155                 160
Pro Arg Gly Glu Arg Gly Glu Ala Gly Pro Ala Gly Lys Asp Gly Glu
                165                 170                 175
```

Arg Gly Pro Val Gly Pro Ala Gly Pro Pro Gly Pro Pro Gly Pro Pro
                180                 185                 190

Gly Pro Pro Gly Pro Pro Gly
        195

<210> SEQ ID NO 20
<211> LENGTH: 614
<212> TYPE: DNA
<213> ORGANISM: Artificial Sequence
<220> FEATURE:
<223> OTHER INFORMATION: Synthetic DNA

<400> SEQUENCE: 20
ccatgggcca tcatcatcac catcacgcag acgaacaaga gaaaaggcc aaagtgcgca      60 ccgaactgat tcaagaatta gcccaaggtt taggtggcat cgagaagaaa aactttccga     120
ctttaggcga tgaggatctg accacacct acatgaccaa gctgctgacc tatttacaag     180
aacgcgaaca agctgaaaat agctggcgca acgtttact gaagggtatt caagatcacg      240
ctttagatct ggttccgcgt ggctcccccg gccctccggg tcccccggt ccccccggtc      300 cgcccggtcc tccggtcct cgcggtgaac aaggcccgca aggtttaccg ggtaaagacg      360
gtgaagccgg tgcacaaggt ccggctggtc cgatgggccc ggctggttc ccgggcgagc      420 gtggtgagaa aggtgagccg gcacccaag gtgctaaagg tgaccgtggt gaaaccggtc      480
ccgttggtcc tcgtggcgag cgcggtgaag ctggtcccgc tggtaaagac ggcgagcgcg     540
gtcccgttgg tccggccggc ccccgggcc cgcccggtcc gccgggcccc cccggtcccc      600
ccggttaagg atcc                                                       614

<210> SEQ ID NO 21
<211> LENGTH: 280
<212> TYPE: PRT
<213> ORGANISM: Artificial Sequence
<220> FEATURE:
<223> OTHER INFORMATION: Protein translated from synthetic DNA

<400> SEQUENCE: 21

His His His His His His Ala Asp Glu Gln Glu Glu Lys Ala Lys Val
1               5                   10                  15

Arg Thr Glu Leu Ile Gln Glu Leu Ala Gln Gly Leu Gly Gly Ile Glu
            20                  25                  30

Lys Lys Asn Phe Pro Thr Leu Gly Asp Glu Asp Leu Asp His Thr Tyr
        35                  40                  45

Met Thr Lys Leu Leu Thr Tyr Leu Gln Glu Arg Glu Gln Ala Glu Asn
    50                  55                  60

Ser Trp Arg Lys Arg Leu Leu Lys Gly Ile Gln Asp His Ala Leu Asp
65                  70                  75                  80

Leu Val Pro Arg Gly Ser Pro Gly Pro Pro Gly Pro Gly Pro Pro
                85                  90                  95

Gly Pro Pro Gly Pro Pro Gly Pro Arg Gly Glu Gln Gly Pro Gln Gly
            100                 105                 110

Leu Pro Gly Lys Asp Gly Glu Ala Gly Ala Gln Gly Pro Ala Gly Pro
        115                 120                 125

Met Gly Pro Ala Gly Phe Pro Gly Glu Arg Gly Glu Lys Gly Glu Pro
    130                 135                 140

Gly Thr Gln Gly Ala Lys Gly Asp Arg Gly Glu Thr Gly Pro Val Gly
145                 150                 155                 160

```
Pro Arg Gly Glu Arg Gly Glu Ala Gly Pro Ala Gly Lys Asp Gly Glu
            165                 170                 175
Arg Gly Pro Val Gly Pro Ala Gly Pro Arg Gly Glu Gln Gly Pro Gln
        180                 185                 190
Gly Leu Pro Gly Lys Asp Gly Glu Ala Gly Ala Gln Gly Pro Ala Gly
            195                 200                 205
Pro Met Gly Pro Ala Gly Phe Pro Gly Glu Arg Gly Glu Lys Gly Glu
    210                 215                 220
Pro Gly Thr Gln Gly Ala Lys Gly Asp Arg Gly Glu Thr Gly Pro Val
225                 230                 235                 240
Gly Pro Arg Gly Glu Arg Gly Glu Ala Gly Pro Ala Gly Lys Asp Gly
            245                 250                 255
Glu Arg Gly Pro Val Gly Pro Ala Gly Pro Pro Gly Pro Pro Gly Pro
            260                 265                 270
Pro Gly Pro Pro Gly Pro Pro Gly
        275                 280

<210> SEQ ID NO 22
<211> LENGTH: 857
<212> TYPE: DNA
<213> ORGANISM: Artificial Sequence
<220> FEATURE:
<223> OTHER INFORMATION: Synthetic DNA

<400> SEQUENCE: 22
ccatgggcca tcatcatcac catcacgcag acgaacaaga agaaaaggcc aaagtgcgca      60
ccgaactgat tcaagaatta gcccaaggtt taggtggcat cgagaagaaa aactttccga     120
ctttaggcga tgaggatctg accacacct acatgaccaa gctgctgacc tatttacaag      180
aacgcgaaca agctgaaaat agctggcgca acgtttact gaagggtatt caagatcacg      240
ctttagatct ggttccgcgt ggctccccg gccctccggg tccccccggt ccccccggtc      300
cgcccggtcc tcccggtcct cgtggtgaac aaggtcctca aggtctgccc ggtaaggatg     360
gtgaagctgg tgcccaaggt ccggccggcc cgatgggccc cgctggtttt ccgggcgaac     420
gcggcgaaaa gggtgaaccg gtacacaag gtgcaaaagg cgatcgtggc gagaccggtc      480
cggtcggtcc ccgcggtgaa cgtggcgagg ctggtcccgc tggtaaagat ggtgagcgtg     540
gcccggttgg tcccgctggt cctcgcggtg aacaaggccc gcaaggttta ccgggtaaag     600
acggtgaagc cggtgcacaa ggtccggctg gtccgatggg cccggctggt ttcccgggcg     660
agcgtggtga aaaggtgag ccgggcaccc aaggtgctaa aggtgaccgt ggtgaaaccg      720
gtcccgttgg tcctcgtggc gagcgcggtg aagctggtcc cgctggtaaa gacggcgagc     780
gcggtcccgt tggtccggcc ggccccccgg gcccgcccgg tccgccgggc cccccggtc      840
cccccggtta aggatcc                                                    857

<210> SEQ ID NO 23
<211> LENGTH: 19
<212> TYPE: DNA
<213> ORGANISM: Artificial Sequence
<220> FEATURE:
<223> OTHER INFORMATION: Synthetic DNA

<400> SEQUENCE: 23
ctcgagggat ccgaattca                                                   19

<210> SEQ ID NO 24
<211> LENGTH: 19
```

```
<212> TYPE: DNA
<213> ORGANISM: Artificial Sequence
<220> FEATURE:
<223> OTHER INFORMATION: Synthetic DNA

<400> SEQUENCE: 24
gagctccatg ggcactttg                                              19

<210> SEQ ID NO 25
<211> LENGTH: 169
<212> TYPE: PRT
<213> ORGANISM: Artificial Sequence
<220> FEATURE:
<223> OTHER INFORMATION: Protein translated from synthetic DNA

<400> SEQUENCE: 25

His His His His His His Ala Asp Glu Gln Glu Glu Lys Ala Lys Val
1               5                   10                  15

Arg Thr Glu Leu Ile Gln Glu Leu Ala Gln Gly Leu Gly Gly Ile Glu
            20                  25                  30

Lys Lys Asn Phe Pro Thr Leu Gly Asp Glu Asp Leu Asp His Thr Tyr
        35                  40                  45

Met Thr Lys Leu Leu Thr Tyr Leu Gln Glu Arg Glu Gln Ala Glu Asn
50                  55                  60

Ser Trp Arg Lys Arg Leu Leu Lys Gly Ile Gln Asp His Ala Leu Asp
65                  70                  75                  80

Leu Val Pro Arg Gly Ser Pro Gly Pro Arg Gly Glu Gln Pro Gln
            85                  90                  95

Gly Leu Pro Gly Lys Asp Gly Glu Ala Gly Ala Gln Gly Pro Ala Gly
            100                 105                 110

Pro Met Gly Pro Ala Gly Phe Pro Gly Glu Arg Gly Glu Lys Gly Glu
            115                 120                 125

Pro Gly Thr Gln Gly Ala Lys Gly Asp Arg Gly Glu Thr Gly Pro Val
130                 135                 140

Gly Pro Arg Gly Glu Arg Gly Glu Ala Gly Pro Ala Gly Lys Asp Gly
145                 150                 155                 160

Glu Arg Gly Pro Val Gly Pro Ala Gly
                165

<210> SEQ ID NO 26
<211> LENGTH: 524
<212> TYPE: DNA
<213> ORGANISM: Artificial Sequence
<220> FEATURE:
<223> OTHER INFORMATION: Synthetic DNA

<400> SEQUENCE: 26
ccatgggcca tcatcatcat caccacgccg atgaacaaga agagaaagca aaggtgcgca       60
ccgaactgat tcaagaactg gcacaaggtc tgggcggtat cgaaaagaag aacttcccga      120
ctttaggtga tgaggattta gatcacacct acatgaccaa actgctgacc tatttacaag      180
aacgcgaaca agctgaaaat agctggcgca aacgtctgct gaaaggcatc caagatcatg      240
cactggatct ggttccgcgt ggtagccccg gtcctcgcgg tgaacaaggt ccgcaaggtc      300
tgccgggtaa agatggtgaa gccggtgcac aaggtccggc tggtcctatg ggcccggccg      360
gctttccggg cgaacgtggt gaaaaaggcg aaccgggtac ccaaggtgcc aaaggtgatc      420
gtggcgaaac cggtccggtt ggccctcgtg gcgaacgcgg tgaagctggt ccggctggca      480
aagacggtga acgtggtccc gttggtccgg ccggttaagg atcc                      524
```

<210> SEQ ID NO 27
<211> LENGTH: 199
<212> TYPE: PRT
<213> ORGANISM: Artificial Sequence
<220> FEATURE:
<223> OTHER INFORMATION: Protein translated from synthetic DNA

<400> SEQUENCE: 27

```
His His His His His His Ala Asp Glu Gln Glu Glu Lys Ala Lys Val
1               5                   10                  15

Arg Thr Glu Leu Ile Gln Glu Leu Ala Gln Gly Leu Gly Gly Ile Glu
            20                  25                  30

Lys Lys Asn Phe Pro Thr Leu Gly Asp Glu Asp Leu Asp His Thr Tyr
        35                  40                  45

Met Thr Lys Leu Leu Thr Tyr Leu Gln Glu Arg Glu Gln Ala Glu Asn
 50                  55                  60

Ser Trp Arg Lys Arg Leu Leu Lys Gly Ile Gln Asp His Ala Leu Asp
 65                  70                  75                  80

Leu Val Pro Arg Gly Ser Pro Gly Pro Pro Gly Pro Pro Gly Pro Pro
                85                  90                  95

Gly Pro Pro Gly Pro Pro Gly Pro Pro Gly Pro Pro Gly Pro Pro Gly
            100                 105                 110

Pro Pro Gly Pro Pro Gly Pro Arg Gly Glu Gln Gly Pro Gln Gly Leu
        115                 120                 125

Pro Gly Lys Asp Gly Glu Ala Gly Ala Gln Gly Pro Ala Gly Pro Met
130                 135                 140

Gly Pro Ala Gly Phe Pro Gly Glu Arg Gly Glu Lys Gly Glu Pro Gly
145                 150                 155                 160

Thr Gln Gly Ala Lys Gly Asp Arg Gly Glu Thr Gly Pro Val Gly Pro
                165                 170                 175

Arg Gly Glu Arg Gly Glu Ala Gly Pro Ala Gly Lys Asp Gly Glu Arg
            180                 185                 190

Gly Pro Val Gly Pro Ala Gly
        195
```

<210> SEQ ID NO 28
<211> LENGTH: 614
<212> TYPE: DNA
<213> ORGANISM: Artificial Sequence
<220> FEATURE:
<223> OTHER INFORMATION: Synthetic DNA

<400> SEQUENCE: 28

| | | | | | |
|---|---|---|---|---|---|
| ccatgggcca | tcatcatcat | caccacgccg | atgagcaaga | agaaaaggcc | aaggttcgca | 60 |
| ccgaactgat | tcaagaactg | gcccaaggtc | tgggtggcat | cgagaaaaag | aacttcccga | 120 |
| ctttaggcga | cgaagattta | gaccacacct | atatgaccaa | gctgctgacc | tatttacaag | 180 |
| aacgcgaaca | agctgaaaac | agttggcgta | aacgtttact | gaagggtatc | caagatcacg | 240 |
| cactggatct | ggttccgcgt | ggttctcccg | gtccccccgg | ccccccggt | ccccccggtc | 300 |
| ccccggtcc | tcccggcccc | cccggtcccc | cggtcctcc | gggtccccc | ggtccgcccg | 360 |
| gtccccgtgg | tgaacaaggc | ccgcaaggtt | taccgggcaa | agacggtgaa | gctggtgcac | 420 |
| aaggtccggc | tggtcctatg | ggcccggccg | gttttccggg | tgagcgtggt | gaaaaaggcg | 480 |
| aaccgggcac | acaaggcgca | aaggtgatc | gcggtgaaac | cggccccgtt | ggccctcgtg | 540 |

```
gcgaacgtgg cgaagctggt ccggccggca agatggtga gcgtggcccc gttggccccg    600
ctggctaagg atcc                                                    614
```

```
<210> SEQ ID NO 29
<211> LENGTH: 199
<212> TYPE: PRT
<213> ORGANISM: Artificial Sequence
<220> FEATURE:
<223> OTHER INFORMATION: Protein translated from synthetic DNA

<400> SEQUENCE: 29
```

```
His His His His His His Ala Asp Glu Gln Glu Glu Lys Ala Lys Val
1               5                   10                  15

Arg Thr Glu Leu Ile Gln Glu Leu Ala Gln Gly Leu Gly Gly Ile Glu
            20                  25                  30

Lys Lys Asn Phe Pro Thr Leu Gly Asp Glu Asp Leu Asp His Thr Tyr
        35                  40                  45

Met Thr Lys Leu Leu Thr Tyr Leu Gln Glu Arg Glu Gln Ala Glu Asn
    50                  55                  60

Ser Trp Arg Lys Arg Leu Leu Lys Gly Ile Gln Asp His Ala Leu Asp
65                  70                  75                  80

Leu Val Pro Arg Gly Ser Pro Gly Pro Arg Gly Glu Gln Gly Pro Gln
                85                  90                  95

Gly Leu Pro Gly Lys Asp Gly Glu Ala Gly Ala Gln Gly Pro Ala Gly
            100                 105                 110

Pro Met Gly Pro Ala Gly Phe Pro Gly Glu Arg Gly Glu Lys Gly Glu
        115                 120                 125

Pro Gly Thr Gln Gly Ala Lys Gly Asp Arg Gly Glu Thr Gly Pro Val
    130                 135                 140

Gly Pro Arg Gly Glu Arg Gly Glu Ala Gly Pro Ala Gly Lys Asp Gly
145                 150                 155                 160

Glu Arg Gly Pro Val Gly Pro Ala Gly Pro Gly Pro Pro Gly Pro
                165                 170                 175

Pro Gly Pro Pro Gly Pro Pro Gly Pro Pro Gly Pro Pro Gly Pro Pro
            180                 185                 190

Gly Pro Pro Gly Pro Pro Gly
        195
```

```
<210> SEQ ID NO 30
<211> LENGTH: 614
<212> TYPE: DNA
<213> ORGANISM: Artificial Sequence
<220> FEATURE:
<223> OTHER INFORMATION: Synthetic DNA

<400> SEQUENCE: 30
ccatgggcca tcatcatcat caccacgccg atgagcaaga agaaaaggcc aaggttcgca    60
ccgaactgat tcaagaactg gcccaaggtc tgggtggcat cgagaaaaag aacttcccga   120
ctttaggcga cgaagattta gaccacacct atatgaccaa gctgctgacc tatttacaag   180
aacgcgaaca gctgaaaaac agttggcgta acgtttact gaagggtatc caagatcacg   240
cactggatct ggttccgcgt ggttctccg gtccgcgtgg cgaacaaggt cctcaaggtt   300
taccgggtaa agatggcgaa gccggtgcac aaggtcccgc tggtcctatg ggtcccgctg   360 gtttcccgg tgaacgcggc gaaaaggtg aacccgtac caaggtgca agggtgacc   420 gtggtgagac cggtcccgtt ggccctcgtg gtgaacgtgg tgaagccggt ccggctggta   480
```

```
aagacggcga gcgcggcccg gttggcccccg ctggccccccc cggtcccccc ggtccccccg    540
gtcctcccgg tccccccggt ccgcccggtc ccccggtccc ccccggtccc cccggtcctc    600
cgggctaagg atcc                                                       614
```

<210> SEQ ID NO 31
<211> LENGTH: 199
<212> TYPE: PRT
<213> ORGANISM: Artificial Sequence
<220> FEATURE:
<223> OTHER INFORMATION: Protein translated from synthetic DNA

<400> SEQUENCE: 31

```
His His His His His His Ala Asp Glu Gln Glu Glu Lys Ala Lys Val
1               5                   10                  15

Arg Thr Glu Leu Ile Gln Glu Leu Ala Gln Gly Leu Gly Gly Ile Glu
            20                  25                  30

Lys Lys Asn Phe Pro Thr Leu Gly Asp Glu Asp Leu Asp His Thr Tyr
        35                  40                  45

Met Thr Lys Leu Leu Thr Tyr Leu Gln Glu Arg Glu Gln Ala Glu Asn
    50                  55                  60

Ser Trp Arg Lys Arg Leu Leu Lys Gly Ile Gln Asp His Ala Leu Asp
65                  70                  75                  80

Leu Val Pro Arg Gly Ser Pro Gly Pro Arg Gly Glu Gln Gly Pro Gln
                85                  90                  95

Gly Leu Pro Gly Lys Asp Gly Glu Ala Gly Ala Gln Gly Pro Ala Gly
            100                 105                 110

Pro Met Gly Pro Ala Gly Phe Pro Gly Glu Arg Gly Glu Lys Gly Glu
        115                 120                 125

Pro Gly Pro Pro Gly Pro Pro Gly Pro Pro Gly Pro Pro Gly Pro Pro
    130                 135                 140

Gly Pro Pro Gly Pro Pro Gly Pro Pro Gly Pro Pro Gly Pro Pro Gly
145                 150                 155                 160

Thr Gln Gly Ala Lys Gly Asp Arg Gly Glu Thr Gly Pro Val Gly Pro
                165                 170                 175

Arg Gly Glu Arg Gly Glu Ala Gly Pro Ala Gly Lys Asp Gly Glu Arg
            180                 185                 190

Gly Pro Val Gly Pro Ala Gly
        195
```

<210> SEQ ID NO 32
<211> LENGTH: 614
<212> TYPE: DNA
<213> ORGANISM: Artificial Sequence
<220> FEATURE:
<223> OTHER INFORMATION: Synthetic DNA

<400> SEQUENCE: 32

```
ccatgggcca tcatcaccat caccatgccg atgagcaaga agaaaaagcc aaagtgcgca    60
ccgaactgat ccaagaactg gcacaaggtc tgggtggcat cgagaagaaa aacttcccga    120
ctttaggcga tgaagattta gaccacacct acatgaccaa actgctgacc tatttacaag    180
aacgtgagca agctgagaat agctggcgca agcgtttact gaaaggcatt caagatcatg    240
ctttagattt agttccgcgt ggtagtccgg gtccgcgtgg tgaacaaggt cctcaaggtc    300
tgccgggtaa agacggtgaa gctggtgccc aaggcccggc tggtccgatg ggtcccgctg    360
gttttccggg cgaacgtggt gaaaaaggtg aacccggtcc cccgggtcct cccggtccgc    420
```

```
cgggcccgcc cggtcccccc ggtccgcccg gtccccggg ccccccggt cctcccggcc     480 ctccgggtac ccaaggtgcc aaaggtgatc gtggtgaaac tggtccggtt ggtcctcgcg     540
gtgaacgcgg cgaagctggt cccgctggta agatggtga gcgcggtccc gttggtccgg     600
ctggttaagg atcc                                                       614
```

<210> SEQ ID NO 33
<211> LENGTH: 7
<212> TYPE: PRT
<213> ORGANISM: Artificial sequence
<220> FEATURE:
<223> OTHER INFORMATION: Protein translated from synthetic DNA

<400> SEQUENCE: 33

```
Leu Val Pro Arg Gly Ser Pro
1               5
```